(12) United States Patent
Tian et al.

(10) Patent No.: US 11,407,832 B2
(45) Date of Patent: Aug. 9, 2022

(54) RECOMBINANT PROTEIN TARGETING PD-L1 AND VEGF

(71) Applicant: ImmuneOnco Biopharmaceuticals (Shanghai) Co., Ltd., Shanghai (CN)

(72) Inventors: Wenzhi Tian, Shanghai (CN); Song Li, Shanghai (CN)

(73) Assignee: ImmuneOnco Biopharmaceuticals (Shanghai) Inc., Shanghai (CN)

( * ) Notice: Subject to any disclaimer, the term of this patent is extended or adjusted under 35 U.S.C. 154(b) by 227 days.

(21) Appl. No.: 16/699,732

(22) Filed: Dec. 2, 2019

(65) Prior Publication Data
US 2020/0172623 A1 Jun. 4, 2020

Related U.S. Application Data

(60) Provisional application No. 62/774,849, filed on Dec. 3, 2018.

(51) Int. Cl.
| | | |
|---|---|---|
| *C07K 16/28* | (2006.01) | |
| *A61P 35/00* | (2006.01) | |
| *C07K 14/71* | (2006.01) | |
| *A61K 38/00* | (2006.01) | |
| *A61K 39/00* | (2006.01) | |

(52) U.S. Cl.
CPC .......... *C07K 16/2827* (2013.01); *A61P 35/00* (2018.01); *C07K 14/71* (2013.01); *A61K 38/00* (2013.01); *A61K 2039/505* (2013.01); *C07K 2317/31* (2013.01); *C07K 2317/732* (2013.01); *C07K 2319/30* (2013.01)

(58) Field of Classification Search
None
See application file for complete search history.

(56) References Cited

FOREIGN PATENT DOCUMENTS

| WO | 2015200905 A2 | 12/2015 |
| WO | 2017136562 A2 | 8/2017 |
| WO | 2019062642 A1 | 4/2019 |
| WO | 2019168947 A1 | 9/2019 |

OTHER PUBLICATIONS

ISA/CN, International search report and written opinion of PCT/CN2019/122446, the counterpart international application, dated Mar. 4, 2020.

*Primary Examiner* — Elly-Gerald Stoica
(74) *Attorney, Agent, or Firm* — Duane Morris LLP; Thomas J. Kowalski; Deborah L. Lu

(57) ABSTRACT

Disclosed is a recombinant protein containing 1) an anti-PD-L1 antibody heavy chain and an anti-PD-L1 antibody light chain, which two are linked by a disulfide bond to bind PD-L1, and 2) an extracellular Ig-like domain of a vascular epithelial growth factor receptor (VEGFR), linked via a linker to the N-terminus or C-terminus of the heavy chain or the light chain, wherein the recombinant protein is capable of binding PD-L1, VEGF and Fc receptor simultaneously. Also disclosed are a recombinant antibody containing two recombinant proteins of the disclosure, a polynucleotide encoding the recombinant protein, an expression vector containing the polynucleotide, a method for producing the recombinant protein and a method for treating a disease caused by over expression of VEGF and/or PD-L1 using the recombinant protein.

8 Claims, 4 Drawing Sheets
Specification includes a Sequence Listing.

RECOMBINANT PROTEIN TARGETING PD-L1 AND VEGF

FIELD OF THE INVENTION

The disclosure relates to a recombinant protein/antibody, and the preparation and use thereof, especially its use in tumor therapies.

BACKGROUND OF THE INVENTION

Cancer cells have developed several mechanisms to evade a host's immune surveillance. For example, many tumor or cancer cells express on their surfaces a high level of PD-L1 and PD-L2, both of which bind to PD-1 on the surface of T cells, inducing T cell apoptosis.

In addition, growth of cancer cells depends on sufficient supply of nutrition. Cancer cells themselves can secrete factors that promote blood vessel growth, such as vascular epithelial growth factors (VEGF). Inhibition of the activity of VEGF or its receptors will stop blood supply to a solid tumor, thereby inhibiting its growth.

PD-L1 and PD-1

PD-L1, also known as programmed death-ligand 1 or CD274, is a transmembrane protein that plays a major role in suppressing the immune system during some particular events such as tissue allografts, autoimmune disease and cancer development.

In certain cancers, the loss of feedback restriction between transcription factors like STAT3 and NF-κB can lead to increased local PD-L1 expression, which could limit the effectiveness of systemic treatment with agents targeting PD-L1 (Vlahopoulos, S A. Aberrant control of NF-κB in cancer permits transcriptional and phenotypic plasticity to curtail dependence on host tissue: molecular mode. Cancer Biology & Bedicine. 2017, 14: 254-270). An analysis of 196 tumor specimens from patients with renal cell carcinoma found that high tumor expression of PD-L1 was associated with increased tumor aggressiveness and a 4.5-fold increased risk of death (Thompson R H, et al. Costimulatory B7-H1 in renal cell carcinoma patients: Indicator of tumor aggressiveness and potential therapeutic target. PNAS. 2004, 101 (49): 17174-9).

PD-1 is a cell surface receptor of about 268 amino acids. When bound with PD-L1 or PD-L2, it down-regulates the immune system and promotes self-tolerance by suppressing T cell inflammatory activity. The inhibitory effect of PD-1 on immune system prevents autoimmune diseases but also prevents the immune system from killing cancer cells. An anti-PD-1 antibody, BMS-936558, produced objective responses in approximately one in five to one in four patients with non-small-cell lung cancer, melanoma, or renal-cell cancer (Suzanne L. Topalian, et al., Safety, Activity, and Immune Correlates of Anti-PD-1 Antibody in Cancer, N Engl J Med 2012, 366:2443-2454).

VEGF and VEGFR

VEGF is a pleiotropic growth factor that is central to control of tissue/wound repair programs, and is classified into VEGF-A, VEGF-B, VEGF-C, VEGF-D and PIGF. During the tissue healing process, VEGF simultaneously drives formation of new blood vessels (angiogenesis) while down-regulating immunity (Canic M, et al. The role of vascular endothelial growth factor in wound healing. J Surg Res. 2009, 153:347-358; Leung D W, et al. Vascular endothelial growth factor is a secreted angiogenic mitogen. Science. 1989, 246:1306-1309; Voron T, et al. Control of the immune response by pro-angiogenic factors. Front Oncol. 2014, 4:70). Both of these properties of VEGF are critical to the oncogenic process, as they enable the development of tumor blood vessels and suppress anticancer immunity Manahan D, Weinberg RA. Hallmarks of cancer: the next generation. Cell. 2011, 144:646-674). In particular, VEGF is thought to exert its immune-suppressive effects via three key mechanisms: inhibiting DC maturation, reducing T cell tumor infiltration, and increasing inhibitory cells in tumor microenvironment. Abnormal VEGF expression also contributes to other diseases, including rheumatoid arthritis, diabetic retinopathy, wet form age-related macular degeneration, and glomerular hypertrophy. Avastin, an FDA approved anti-VEGF monoclonal antibody drug, functions to treat cancers (colon cancer, lung cancer) by inhibiting the biological activities of VEGF. Another protein drug targeting VEGF, Aflibercept, was approved in United State and Europe for treatment of wet macular degeneration under tradename Eylea, and for metastatic colorectal cancer as Zaltrap.

VEGF receptor (VEGFR) has three subtypes, VEGFR-1, VEGFR-2 and VEGFR-3, all having an extracellular portion consisting of 7 immunoglobulin-like domains, a single transmembrane region and an intracellular portion. VEGFR-2 appears to mediate almost all of the known cellular responses to VEGFs, while VEGFR-1 sequesters VEGF from VEGFR-2 binding and modulates VEGFR-2 signaling. VEGF-A, the most dangerous type to human health, binds to both VEGFR-1 and VEGFR-2. VEGFR antagonists are mostly used, or under investigation, for treating cancers. Lenvima, acting as a multiple kinase inhibitor against VEGFR-1, VEGFR-2 and VEGFR-3 kinases, was approved in 2015 for the treatment of differentiated thyroid cancer, and in 2016 for treatment of advanced renal cell carcinoma in combination with Everolimus.

Fc and FcR

The fragment crystallizable region (Fc region) is the tail region of an antibody and is the domain that determines the effector function of the antibody, that is, how it engages with specific cell receptors or other defense proteins.

An Fc receptor (FcR) is a protein found on the surface of certain immune effector cells, including B lymphocytes, follicular dendritic cells, natural killer cells, macrophages, neutrophils, eosinophils, basophils, and mast cells. These cells contribute to the protective functions of the immune system.

An Fc region may interact with Fc receptors and/or proteins of the complement system, activating the immune system. For example, Fc receptors bind to antibodies that are attached to infected cells or invading pathogens, stimulating phagocytic or cytotoxic cells to destroy microbes, or infected cells by antibody-mediated phagocytosis or antibody-dependent cell-mediated cytotoxicity (ADCC).

Therapeutic Bi-Specific or Multi-Specific Fusion Proteins/Antibodies

Protein/antibody therapies have significantly advanced our abilities to treat diseases, including cancers, yet clinical studies have shown that many patients do not adequately respond to monospecific therapy. For example, among patients treated with antibodies targeting PD-L1/PD-1, only a subset experience durable response and/or survival. Two VEGF targeting proteins mentioned above, Avastin and Aflibercept, inhibit cancer cell growth to certain extent but cannot eliminate the cancer cells.

To address the above limitations, bi-specific or multi-specific recombinant proteins are developed against two or more separate and different antigens, or different epitopes of the same antigen. For example, some bispecific proteins are engineered to simultaneously bind a cytotoxic cell and a tumor cell to be destroyed. Such proteins are capable of blocking multiple tumor cell growth and survival pathways, and/or activating tumor cell killing pathways, having a potential to better inhibit cancer growth.

However, bispecific or multi-specific proteins, especially bispecific or multi-specific antibodies, present significant design challenges, because a large number of variables have to be considered, including compatibility of the molecules, whether they can be linked together, and affinity, stability and pharmaceutical properties of the resulting proteins even if they can be linked physically. It is well recognized that simply linking two or more antibodies or proteins together often does not result in synergetic or even advantageous effects. A recombinant antibody disclosed in the Comparative Example below, comprising SIRPαD1, linked by a linker, to an anti-EGFR antibody, has been proved to have inferior anti-tumor activity compared to the anti-EGFR antibody or SIRPαD1-Fc alone in the HT-29 or NCl-H1975 tumor model.

SUMMARY OF THE INVENTION

Through diligent efforts, the present inventors have successfully designed a recombinant protein and a recombinant antibody that target both PD-L1 and VEGF and at the same time binds to FcR. The recombinant protein/antibody of the present disclosure shows better anti-tumor activity than its mono-specific counterparts, even if they are used in combination.

Accordingly, in a first aspect, the present disclosure provides a recombinant protein comprising an anti-PD-L1 antibody heavy chain and an anti-PD-L1 antibody light chain, which two are linked by a disulfide bond to bind PD-L1, and an extracellular Ig-like domain of a vascular epithelial growth factor receptor (VEGFR), linked via a linker to the N-terminus or C-terminus of the heavy chain or the light chain, wherein the recombinant protein is capable of binding PD-L1, VEGF and Fc receptor simultaneously.

In some embodiments, the extracellular Ig-like domain of VEGFR is linked via a linker to the N-terminus of the heavy chain. In some embodiments, the extracellular Ig-like domain of VEGFR is linked via a linker to the C-terminus of the heavy chain. In some embodiments, the extracellular Ig-like domain of VEGFR is linked via a linker to the N-terminus of the light chain.

Also provided is a dimer comprising the recombinant protein described herein. The dimer may be a homodimer comprising two recombinant proteins described above, such as two identical ones.

In a second aspect, the present disclosure provides a recombinant antibody, comprising an anti-PD-L1 antibody having two heavy chains and two light chains, wherein an extracellular Ig-like domain of a vascular epithelial growth factor receptor (VEGFR) is linked via a linker to N-terminus or C-terminus of each heavy chain, or to N-terminus or C-terminus of each light chain, wherein the recombinant antibody is capable of binding PD-L1, VEGF and FcR simultaneously. The recombinant antibody is a homodimer of the recombinant protein described in the first aspect.

In some embodiments, the extracellular Ig-like domain of VEGFR is linked via a linker to the N-terminus of each heavy chain. In some embodiments, the extracellular Ig-like domain of VEGFR is linked via a linker to the C-terminus of each heavy chain. In some embodiments, the extracellular Ig-like domain of VEGFR is linked via a linker to the N-terminus of each light chain.

Binding to PD-L1 on target cells such as cancer cells releases the check on T cells by PD-1-mediated inhibitory signals, while binding to VEGF prohibits new blood vessel formation and releases immunity suppression and thus limit target cell growth. Further, binding to FcR on immune cells such as NK cells or macrophages stimulates targeted cell killings by NK cells or macrophages.

The anti-PD-L1 antibody describe in the first aspect and the second aspect may be an isolated monoclonal antibody such as Atezolizumab, Avelumab, Durvalumab, and an antibody having at least 80%, 85%, 90%, 95%, 98% or 99% amino acid identity to Atezolizumab, Avelumab, or Durvalumab.

The anti-PD-L1 antibody may be an isolated monoclonal antibody, comprising two heavy chains each having an amino acid sequence of SEQ ID NO: 2 or 4, and two light chains each having an amino acid sequence of SEQ ID NO: 6, which may be encoded by nucleic acid sequences of SEQ ID NOs: 1, 3 and 5, respectively. The antigen-binding (Fab) portion (or paratope) of the anti-PD-L1 antibody can bind to PD-L1 on the cell surfaces of target cells such as cancer/tumor cells to block the interaction of PD-L1 with PD-1 on the cell surfaces of T cells and thus release the check on T cells by PD-1-mediated inhibitory signals. The Fc portion of the anti-PD-L1 antibody can bind to FcRs on the cell surfaces of immune cells such as NK cells and macrophages to stimulate targeted cell killings by the NK cells or macrophages.

In some embodiments, the heavy chain of the anti-PD-L1 antibody may comprise an amino acid sequence having at least 80%, 85%, 90%, 95%, 98% or 99% identity to SEQ ID NO: 2, wherein the anti-PD-L1 antibody is able to bind to PD-L1 and block the interaction of PD-L1 with PD-1 on the cell surfaces of T cells, and is also able to bind to FcRs on the cell surfaces of immune cells and thus activate these cells for killing target cells such as cancer cells.

In some embodiments, the light chain may comprise an amino acid sequence having at least 80%, 85%, 90%, 95%, 98% or 99% identity to SEQ ID NO: 6, wherein the anti-PD-L1 antibody is able to bind to PD-L1 and block the interaction of PD-L1 with PD-1 on the cell surfaces of T cell, and is also able to bind to FcRs on the cell surfaces of immune cells and thus activate these cells for killing target cells such as cancer cells.

The VEGFR describe in the first aspect and the second aspect may be VEGFR1 and/or VEGFR2, and the extracellular Ig-like domain of the VEGFR may be the second extracellular Ig-like domain of the VEGFR. In one embodiment, the VEGFR is VEGFR1, and the extracellular Ig-like domain of VEGFR1 is the second extracellular Ig-like domain of VEGFR1 (VEGFR1D2). In another embodiment, the VEGFR is VEGFR2, and the extracellular Ig-like domain of VEGFR2 is the second extracellular Ig-like domain of VEGFR2 (VEGFR2D2). The extracellular Ig-like domain of the VEGFR can bind to VEGFs expressed by or around target cells, for instance, cancer/tumor cells, and thus limit growth of target cells.

In one embodiment, the VEGFR1D2 has a nucleic acid sequence and an amino acid sequence set forth in SEQ ID NOs: 7 and 8, respectively. In some embodiments, the VEGFR1D2 may comprise an amino acid sequence having at least 80%, 85%, 90%, 95%, 98% or 99% identity to SEQ ID NO: 8, wherein the VEGFR1D2 can bind to VEGFs expressed by or around target cells, for instance, cancer/tumor cells and thus limit growth of target cells.

The linker described in the first aspect and the second aspect may be a peptide of about 5 to 30 amino acid residues. In an embodiment, the linker is a peptide of 10 to 30 amino acid residues. In another embodiment, the linker is a peptide of 10 to 15 amino acid residues. In some embodiments, the linker is —(Gly-Gly-Gly-Gly-Ser)$_2$-(SEQ ID NO: 10) or -(Gly-Gly-Gly-Gly-Ser)$_3$-(SEQ ID NO: 12), which may be encoded by SEQ ID NO: 9 and 11, respectively.

The VEGFR1D2-Linker-anti-PD-L1 heavy chain, with VEGFR1D2 linked to N-terminus of the anti-PD-L1 heavy chain, comprises an amino acid sequence of SEQ ID NO: 14, which may be encoded by nucleotide of SEQ ID NO: 13. In some embodiments, the VEGFR1D2-Linker-anti-PD-L1 heavy chain comprises an amino acid sequence having at least 80%, 85%, 90%, 95%, 98% or 99% identity to SEQ ID NO: 14, wherein the VEGFR1D2-Linker-anti-PD-L1 heavy chain together with the light chain of the anti-PD-L1 antibody can bind to VEGF, PD-L1 and FcR, i) blocking the interaction of PD-L1 on target cells with PD-1 on T cells; ii) blocking the interaction of VEGF with VEGFR on target cells' surfaces; and iii) stimulating targeted cell killings by immune cells.

The anti-PD-L1 heavy chain-Linker-VEGFR1D2, with VEGFR1D2 linked to C-terminus of the anti-PD-L1 heavy chain, comprises an amino acid sequence of SEQ ID NO: 16, which may be encoded by nucleotide of SEQ ID NO: 15. In some embodiments, the anti-PD-L1 heavy chain-Linker-VEGFR1D2 comprises an amino acid sequence having at least 80%, 85%, 90%, 95%, 98% or 99% identity to SEQ ID NO: 16, wherein the VEGFR1D2-Linker-anti-PD-L1 heavy chain together with the light chain of the anti-PD-L1 antibody can bind to VEGF, PD-L1 and FcR, i) blocking the interaction of PD-L1 on target cells with PD-1 on T cells; ii) blocking the interaction of VEGF with VEGFR on target cells' surfaces; and iii) stimulating targeted cell killings by immune cells.

The VEGFR1D2-Linker-anti-PD-L1 light chain, with VEGFR1D2 linked to N-terminus of the anti-PD-L1 light chain, comprises an amino acid sequence of SEQ ID NO: 18, which may be encoded by nucleotide of SEQ ID NO: 17. In some embodiments, the VEGFR1D2-Linker-anti-PD-L1 light chain comprises an amino acid sequence having at least 80%, 85%, 90%, 95%, 98% or 99% identity to SEQ ID NO: 18, wherein the VEGFR1D2-Linker-anti-PD-L1 light chain together with the heavy chain of the anti-PD-L1 antibody can bind to VEGF, PD-L1, and FcR, i) blocking the interaction of PD-L1 on target cells with PD-1 on T cells; ii) blocking the interaction of VEGF with VEGFR on target cells' surfaces; and iii) stimulating targeted cell killings by immune cells.

In a third aspect, a nucleic acid molecule encoding the recombinant protein/antibody of the present disclosure is also provided, as well as an expression vector comprising the nucleic acid and a host cell comprising the expression vector.

In a fourth aspect, a method for preparing the recombinant protein/antibody using the host cell comprising the expression vector is also provided, the method comprising the steps of (i) expressing the recombinant protein/antibody in the host cell and (ii) isolating the recombinant protein/antibody from the host cell.

In a fifth aspect, the present disclosure provides a pharmaceutical composition, comprising the recombinant protein or the recombinant antibody of the present disclosure, and at least one pharmaceutically acceptable carrier.

In a sixth aspect, the present disclosure provides a method for treating a disease caused by over-expression of VEGF and/or PD-L1, comprising administering to a patient or a subject in need thereof a therapeutically effective amount of the pharmaceutical composition of the present disclosure.

In one embodiment, the present disclosure provides the use of the recombinant protein or the recombinant antibody in the manufacture of a pharmaceutical composition for the treatment of a disease caused by over-expression of VEGF and/or PD-L1.

In one embodiment, the method of the present disclosure is for treating a disease selected from the group consisting of acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, liver cancer, and renal cell carcinoma. In one embodiment, the present disclosure provides a method for treating age-related macular degeneration (AMD), diabetic retinopathy, liver fibrosis or angiosarcoma.

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1:
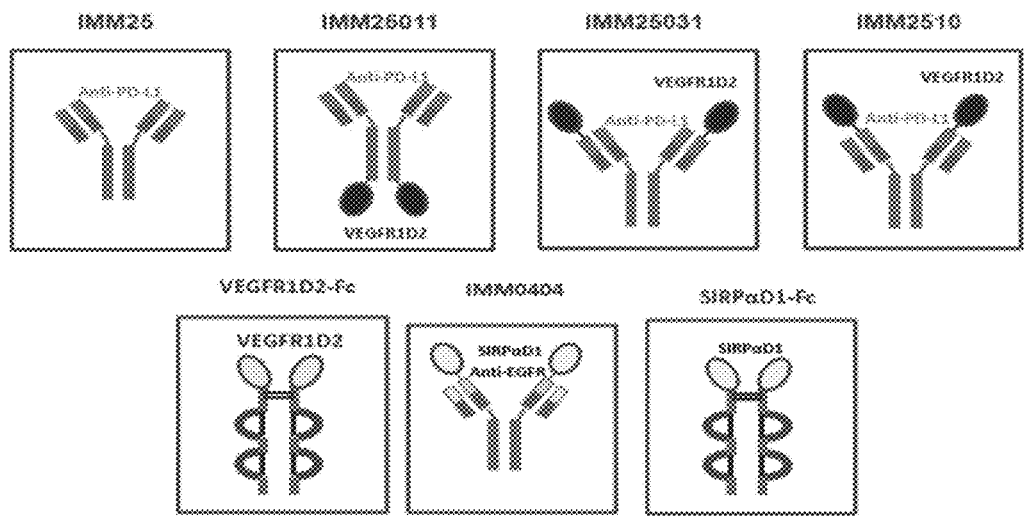
FIG. 1 is a schematic diagram of the structures of recombinant antibodies of the present disclosure.

Antibody therapies are approved in various jurisdictions to treat a wide range of diseases, including cancers, and have significantly improved patient outcomes (Komeev K V et al., (2017) TLR-signaling and proinflammatory cytokines as drivers of tumorigenesis. *Cytokine* 89: 127-135). Once bound to a disease antigen, antibodies may induce antibody-dependent cell-mediated cytotoxicity, activate the complement system, and/or prevent a receptor from interacting with its ligand, all of which may lead to cell death. U.S. FDA-approved antibody drugs include Alemtuzumab, Nivolumab, Rituximab and Durvalumab.

However, clinical studies have shown many patients do not adequately respond to monospecific therapy. For example, the overall response rate of an approved anti-PD-L1 antibody, Avelumab (BAVENCIO), is only 33%. Additionally, acquired antibody resistance frequently occurs following several cycles of treatment.

Therefore, bispecific or multi-specific antibodies are required against two or more separate and unique antigens, or different epitopes of the same antigen.

Through diligent experimentation, the present inventor has invented a novel recombinant protein/antibody, which can attack diseases, via three mechanisms of actions, to release the check or inhibition on T cells by PD-1-mediated inhibitory signals, to prohibit new blood vessel formation and release immunity suppression and thus limit target cell growth, and to stimulate targeted cell killings by immune cells such as NK cells and macrophages.

The recombinant protein of the present disclosure comprises 1) an anti-PD-L1 antibody heavy chain and an anti-PD-L1 antibody light chain, which two are linked by a disulfide bond to bind PD-L1, and 2) an extracellular Ig-like domain of a vascular epithelial growth factor receptor (VEGFR), linked via a linker to the N-terminus or C-terminus of the heavy chain or the light chain, wherein the recombinant protein is capable of binding PD-L1, VEGF and Fc receptor simultaneously. In some embodiments, the extracellular Ig-like domain of VEGFR is linked via a linker to the N-terminus of the heavy chain. In some embodiments, the extracellular Ig-like domain of VEGFR is linked via a linker to the C-terminus of the heavy chain. In some embodiments, the extracellular Ig-like domain of VEGFR is linked via a linker to the N-terminus of the light chain. The Fc fragment of the heavy chain will be linked to another Fc fragment by disulfide bonds. For example, two recombinant proteins of the disclosure will be linked together by disulfide bonds to form the recombinant antibody of the present disclosure.

The recombinant antibody of the disclosure comprises an anti-PD-L1 antibody having two heavy chains and two light chains, wherein an extracellular Ig-like domain of a vascular epithelial growth factor receptor (VEGFR) is linked via a linker to N-terminus or C-terminus of each heavy chain, or to N-terminus or C-terminus of each light chain, wherein the recombinant antibody is capable of binding PD-L1, VEGF and FcR simultaneously. In some embodiments, the extracellular Ig-like domain of VEGFR is linked via a linker to the N-terminus of each heavy chain. In some embodiments, the extracellular Ig-like domain of VEGFR is linked via a linker to the C-terminus of each heavy chain. In some embodiments, the extracellular Ig-like domain of VEGFR is linked via a linker to the N-terminus of each light chain.

The inventors of the present application surprisingly found that the Fc portion of an antibody remains FcR binding capacity even when a polypeptide is linked to the C-terminus of the Fc fragment. In particular, the inventors, in an unpublished study, designed and prepared a recombinant antibody comprising a normal Ig-like antibody and two VEGFR1D2 fragments, wherein the two VEGFR1D2 fragments are linked to two Fc fragments of the antibody, respectively. The recombinant antibody actively lysed target cells in an ADCC assay with a bit lower activity than the normal antibody, the maximum lysis % and lysis $EC_{50}$ were about 45.0% and 68.71 ng/ml for the recombinant antibody, and the maximum lysis % and lysis $EC_{50}$ for the normal antibody were about 58.0% and 49.55 ng/ml. In a later in vivo anti-tumor test, the recombinant antibody showed a better anti-tumor effect than the combined use of the normal antibody and VEGFR1D2-Fc.

The three main components contained in the recombinant protein/antibody of the present disclosure are the extracellular Ig-like domain of a vascular epithelial growth factor receptor (VEGFR), the linker, and the anti-PD-L1 antibody. A person of ordinary skills in the art will recognize that there are many design choices for selecting the above three components. Preferably, human-derived sequence is used in human disease therapies, as the strong immunogenicity of proteins or peptides from non-human animals may lead to allergy and other adverse effects. However, other animal proteins or peptides, humanized if appropriate, may also be used in the present disclosure based on different application purposes.

Any anti-PD-L1 antibody may be used in the formation of the recombinant protein or antibody of the present disclosure. The anti-PD-L1 antibody may be an isolated monoclonal antibody selected from the group consisting of Atezolizumab, Avelumab, and Durvalumab.

In some embodiments, the anti-PD-L1 antibody is an isolated monoclonal antibody comprising two heavy chains each having an amino acid sequence of SEQ ID NO: 2 or 4, and two light chains each having an amino acid sequence of SEQ ID NO: 6, which two may be encoded by nucleic acid sequences of SEQ ID NOs: 1, 3 and 5, respectively. The Fab portion (or paratope) of the anti-PD-L1 antibody can bind to PD-L1 on the cell surfaces of target cells such as tumor/cancer cells to block the interaction of PD-L1 with PD-1 on the cell surfaces of T cells and thus release the check on T cells by PD-1-mediated inhibitory signals, while the Fc portion of the anti-PD-L1 antibody can bind to FcRs on the cell surfaces of immune cells such as NK cells and macrophages to stimulate targeted cell killings by the NK cells or macrophages. In some embodiments, the heavy chain of the anti-PD-L1 antibody may comprise an amino acid sequence having at least 80%, 85%, 90%, 95%, 98% or 99% identity to SEQ ID NO: 2, wherein the anti-PD-L1 antibody is able to bind to PD-L1 and block the interaction of PD-L1 with PD-1 on the cell surfaces of T cells, and is also able to bind to FcRs on the cell surfaces of immune cells and thus activate these cells for killing target cells such as cancer cells. In some embodiments, the light chain may comprise an amino acid sequence having at least 80%, 85%, 90%, 95%, 98% or 99% identity to SEQ ID NO: 6, wherein the anti-PD-L1 antibody is able to bind to PD-L1 and block the interaction of PD-L1 with PD-1 on the cell surfaces of T cells, and is also able to bind to FcRs on the cell surfaces of immune cells and thus activate these cells for killing target cells such as cancer cells.

Any extracellular Ig-like domain of any VEGFR (VEGFR1, VEGFR2, and VEGFR3) capable of binding with VEGF, especially VEGF-A, may be selected for construction of the recombinant protein. In one embodiment, the VEGFR in the recombinant protein is VEGFR1, and the extracellular Ig-like domain of the VEGFR is the second extracellular Ig-like domain of VEGFR1 (VEGFR1D2).

In one embodiment, the VEGFR1D2 has a nucleic acid sequence and an amino acid sequence set forth in SEQ ID Nos: 7 and 8, respectively. In another embodiment, the VEGFR1D2 may comprise an amino acid sequence having at least 80%, 85%, 90%, 95%, 98% or 99% identity to SEQ ID NO: 8, wherein the VEGFR1D2 can bind to VEGFs expressed by or around target cells, for instance, cancer/tumor cells and thus limit growth of target cells.

Linkers serve primarily as a spacer between the extracellular Ig-like domain of VEGFR and the N-terminus or C-terminus of the heavy chain or light chain of an anti-PD-L1 antibody. The linker may be made up of amino acids linked together by peptide bonds, preferably from 5 to 30 amino acids linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, $(Gly)_8$, poly(Gly-Ala), and polyalanines. One exemplary suitable linker as shown in the Examples below is (Gly-Ser), such as —(Gly-Gly-Gly-Gly-Ser)$_3$- and —(Gly-Gly-Gly-Gly-Ser)$_2$-.

Linkers may also be non-peptide linkers. For example, alkyl linkers such as —NH—, —(CH$_2$)s-C(O)—, wherein s=2-20 can be used. These alkyl linkers may further be substituted by any non-sterically hindering group such as lower alkyl (e.g., $C_{1-4}$) lower acyl, halogen (e.g., Cl, Br), CN, NH$_2$, phenyl, etc.

Also, the present disclosure provides a polynucleotide molecule encoding the recombinant protein or antibody and an expression vector expressing the recombinant protein or antibody. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present disclosure provides host cells comprising the above expression vectors. The host cells may be transformed or transfected with the expression vectors. Suitable host cells include *Escherichia coli*, yeasts and other eukaryotes. Preferably, *Escherichia coli*, yeast or mammalian cell lines (such as COS or CHO) are used.

In another aspect, the present disclosure provides a pharmaceutical composition comprising the recombinant protein or antibody of the present disclosure formulated together with a pharmaceutically acceptable carrier. The composition may optionally contain one or more additional pharmaceutically active ingredients, such as another antibody or a drug. The pharmaceutical compositions of the disclosure also can be administered in a combination therapy with, for example, another immune-stimulatory agent, anti-cancer agent, an anti-viral agent, or a vaccine.

The pharmaceutical composition can comprise any number of excipients. Excipients that can be used include carriers, surface active agents, thickening or emulsifying agents, binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: The Science and Practice of Pharmacy, 20th Ed. (Lippincott Williams & Wilkins 2003), the disclosure of which is incorporated herein by reference.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin Other exemplary pharmaceutical compositions comprise Tris buffers, or acetate buffers, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution.

Further, the therapeutic composition may be formulated as a lyophilizate using appropriate excipients such as sucrose.

Preferably, the pharmaceutical composition is suitable for intravenous, intramuscular, subcutaneous, parenteral, spinal or epidermal administration (e.g., by injection or infusion). Depending on the route of administration, the active molecule can be coated in a material to protect it from the action of acids or enzymes and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active molecule calculated to produce the desired therapeutic effect in association with the required pharmaceutical carrier. Alternatively, the recombinant protein can be administered as a sustained release formulation, in which case less frequent administration is required.

For administration of the recombinant protein, the dosage may range from about 0.0001 to 100 mg/kg, and more usually 0.01 to 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Preferred dosage regimens for the recombinant protein of the disclosure include 3 mg/kg body weight or 6 mg/kg body weight via intraperitoneal administration, with the protein being given using one of the following dosing schedules: (i) every four weeks for six dosages, then every three months; (ii) every three weeks; (iii) 3 mg/kg body weight once followed by 1 mg/kg body weight every three weeks; (vi) 6 mg/kg body weight, one dosage per week. In some methods, dosage is adjusted to achieve a plasma antibody concentration of about 1-1000 μg/ml and in some methods about 25-300 μg/ml.

A "therapeutically effective dosage" of a recombinant protein of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects. A therapeutically effective amount of a fusion protein of the present disclosure can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the recombinant protein of the disclosure can be formulated to ensure proper distribution in vivo. For example, to ensure that the therapeutic proteins of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331.

A gene therapy in vivo is also envisioned wherein a nucleic acid molecule encoding the recombinant protein of the present disclosure, or a derivative thereof is introduced directly into the subject. For example, a nucleic acid sequence encoding a recombinant protein of the present disclosure is introduced into target cells via local injection of a nucleic acid construct with or without an appropriate delivery vector, such as an adeno-associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present disclosure is to provide a method for preparing the above recombinant protein or recombinant antibody and the pharmaceutical composition comprising the same. In one embodiment, the method comprises (1) providing a recombinant protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein or antibody. The preparation may be carried out with well-known technologies by an ordinarily skilled artisan.

Another object of the present disclosure is to provide a method of treating diseases using the pharmaceutical composition of the present disclosure, comprising administrating an effective amount of the aforementioned pharmaceutical composition to the patients or subjects in need thereof.

In one embodiment, the pharmaceutical composition is used to treat VEGF and/or PD-L1-overexpressing tumors or cancers, including but not limited to acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, pancreatic cancer, liver cancer and renal cancer.

In one embodiment, the present disclosure provides a method for treating diseases related to over-expressions of VEGF, which include, but not limited to, age-related macular degeneration (AMD), diabetic retinopathy, liver fibrosis and angiosarcoma.

The present disclosure is now further described with the non-limiting examples below.

EXAMPLES

In the descriptions below, IMM25 refers to a monoclonal anti-PD-L1 antibody that targets PD-L1. This antibody has two heavy chains each having an amino acid sequence of SEQ ID NO: 2, and two light chains each having an amino acid sequence of SEQ ID NO: 6.

IMM2510 refers to a recombinant antibody, containing two VEGFR1D2s each linked via a GS-linker, to the N-terminus of each heavy chain of an anti-PD-L1 antibody. The VEGFR1D2-linker-anti-PD-L1 heavy chain is encoded by a nucleic acid sequence of SEQ ID NO: 13, and has an amino acid sequence of SEQ ID NO: 14, respectively. The light chain of the anti-PD-L1 antibody has an amino acid sequence of SEQ ID NO: 6.

IMM25011 refers to a recombinant antibody, containing two VEGFR1D2s each linked via a GS-linker, to the C-terminus of each heavy chain of an anti-PD-L1 antibody. The anti-PD-L1 heavy chain-Linker-VEGFR1D2 is encoded by a nucleic acid sequence of SEQ ID NO: 15, and has an amino acid sequence and SEQ ID NO: 16. The light chain of the anti-PD-L1 antibody has an amino acid sequence of SEQ ID NO: 6.

IMM25031 refers to a recombinant antibody, containing two VEGFR1D2s each linked via a GS-linker, to the N-terminus of each light chain of an anti-PD-L1 antibody. The VEGFR1D2-linker-anti-PD-L1 light chain is encoded by a nucleic acid sequence of SEQ ID NO: 17, and has an amino acid sequence of SEQ ID NO: 18. The heavy chain of the anti-PD-L1 antibody had an amino acid sequence of SEQ ID NO: 2.

VEGFR1-Fc is a recombinant protein, containing two VEGFR1D2s linked to an antibody Fc portion. Each VEGFR1D2-Fc fragment has an amino acid sequence of SEQ ID NO:22, which may be encoded by a nucleic acid sequence of SEQ ID NO:21.

The basic structures of these four recombinant antibodies are shown in FIG. 1.

Example 1

Construction of Vectors Expressing IMM25, IMM25011, IMM25031 and IMM2510

1.1 IMM25

Full-length coding sequence of IMM25 was designed artificially. Specifically, 57 nucleotides encoding the signal peptide of mouse IgG1 heavy chain (SEQ ID NO.: 19) were added to the 5' end of the anti-PD-L1 heavy chain-coding sequence (SEQ ID NO.: 1), and a Kozak sequence (SEQ ID NO: 20) was added to the 5' end of the signal peptide sequence. Lastly, HindIII and NheI restriction sites were added to the 5' and 3' ends of the resulting sequence, respectively. For the light chain, the same signal sequence as well as the Kozac sequence was used, but HindIII and XbaI restriction sites were added to the resulting sequence, respectively. The two resulting sequences were synthesized by Genscript (#: C0015BJ110-1 (heavy chain); C0015BJ110-2 (light chain)) and subcloned, respectively, into the pMac-H and pMac-L vectors.

1.2 IMM2510

Full-length coding sequence of IMM2510 was designed artificially. Specifically, for the heavy chain, the coding sequence of the second extracellular domain of VEGFR1 (VEGFR1D2) (SEQ ID NO.: 7) was linked through the GS-linker (SEQ ID NO.: 11) to the 5' end of the anti-PD-L1 heavy chain coding sequence (SEQ ID NO.:3). 57 nucleotides encoding the signal peptide of mouse IgG1 heavy chain (SEQ ID NO.: 19) were added to the 5' end of VEGFR1D2-coding sequence, and a Kozak sequence (SEQ ID NO.: 20) was added to the 5' end of the signal peptide sequence. Lastly, HindIII and NheI restriction sites were added to the 5' and 3' ends of the resulting sequence, respectively. The resulting sequence was synthesized by Genscript (ID #: C9143DA150-1) and subcloned into the pMac-H vector. The expression vector for the light chain of IMM2510 is identical to that of IMM25.

1.3 IMM25011

Full-length coding sequence of IMM25011 was designed artificially. Specifically, for the heavy chain, the coding sequence of anti-PD-L1 heavy chain coding sequence (SEQ ID NO.:3) was linked through the GS-linker (SEQ ID NO.: 9) to the 3' end of the coding sequence of the second extracellular domain of VEGFR1 (VEGFR1D2) (SEQ ID NO.: 7), and NheI and SalI restriction sites were added to the 5' and 3' ends of the resulting sequence, respectively. The resulting sequence was synthesized by Genscript (ID #: C8379CJ170-1) and subcloned into the IMM25 heavy chain expression vector. The expression vector for the light chain of IMM2510 is identical to that of IMM25.

1.4 IMM25031

Full-length coding sequence of IMM25011 was designed artificially. Specifically, for the light chain, the coding sequence of the second extracellular domain of VEGFR1 (VEGFR1D2) (SEQ ID NO.: 7) was linked through the GS-linker (SEQ ID NO.: 11) to the 5' end terminal of the anti-PD-L1 light chain coding sequence (SEQ ID NO.:5). 57 nucleotides encoding the signal peptide of mouse IgG1 heavy chain (SEQ ID NO.: 19) were added to the 5' end of VEGFR1D2-coding sequence, and a Kozak sequence (SEQ ID NO.: 20) was added to the 5' end of the signal peptide sequence. Lastly, HindIII and XbaI restriction sites were added to the 5' and 3' ends of the resulting sequence, respectively. The resulting sequence was synthesized by Genscript (ID #: C4608CE150-1) and subcloned into the pMac-L vector. The expression vector for the heavy chain of IMM25031 is identical to that of IMM25.

Example 2

Manufacture and Quality Analysis of Recombinant Fusion Antibodies

To manufacture the recombinant proteins, the expression vectors were transfected into Free Style™ CHO-S cells (Thermo Fisher Scientific, Cat #R80007) using Polyetherimide (PEI) (polysciences, Cat #24765-1) as the tranfectant. Cells were cultured for about 7-10 days before harvesting cell culture supernatant for protein purification by affinity chromatography. The purity of the recombinant proteins was analyzed by SEC-HPLC.

Figure 2:
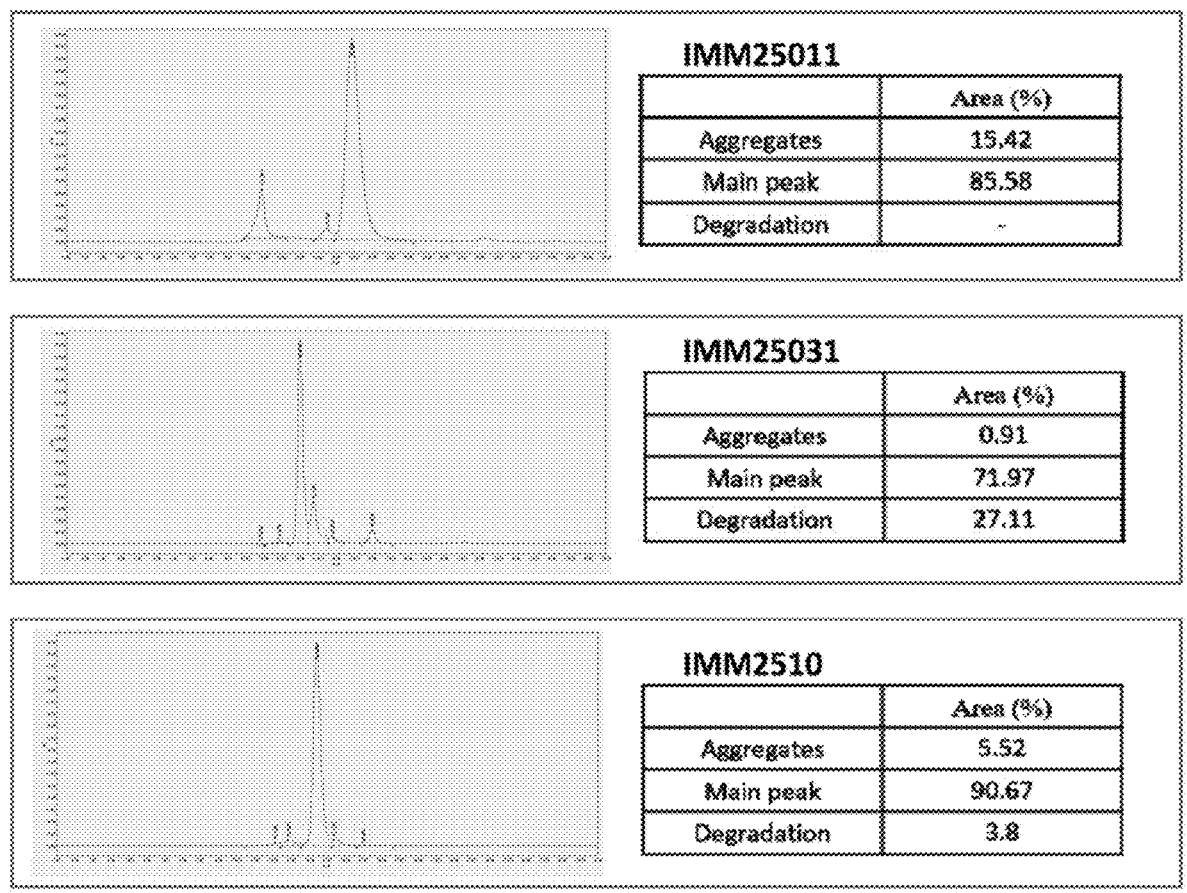
FIG. 2 shows SEC-HPLC diagrams of recombinant antibodies of the present disclosure.

The SEC-HPLC diagram in FIG. 2 showed a big difference among the three recombinant antibodies of the present disclosure. IMM2510 had the highest purity (90.67%), followed by IMM25011 (85.58%) and IMM25031 (71.97%). IMM25011 had high percentage of aggregates (15.42%), while IMM25031 had more degradation (27.11%).

Example 3

Recombinant Antibodies Bound to VEGF-165

For VEGF binding, recombinant human VEGF-165 (Cat #11066-HNAH, Sino Biologicals) was prepared in coating buffer (Product code: 1001329288 C3041-100CAP, Sigma-Aldrich Co.) and transferred to the ELISA plate (Cat #442404, Nunc™) at 50 ng/well, and the plate was placed in 4° C. refrigerator overnight. Then, the plate was washed for three times with PBS containing 0.05% of Tween-20 (PBS-T) before serially diluted recombinant antibodies and control antibody (Avastin) were added, and the plate was incubated at room temperature for 1 hour and then washed again for 5 times with PBS-T. HRP-Rabbit Anti-Human IgG Fc (Cat #:309-036-008, Jackson ImmunoResearch Lab) was added to the plate and the plate was incubated at room for one hour. After washing the plate for 5 times with PBS-T, substrate was added to the plate which was read in a plate reader after the color changing was stopped by 1N $H_2SO_4$.

Figure 3:
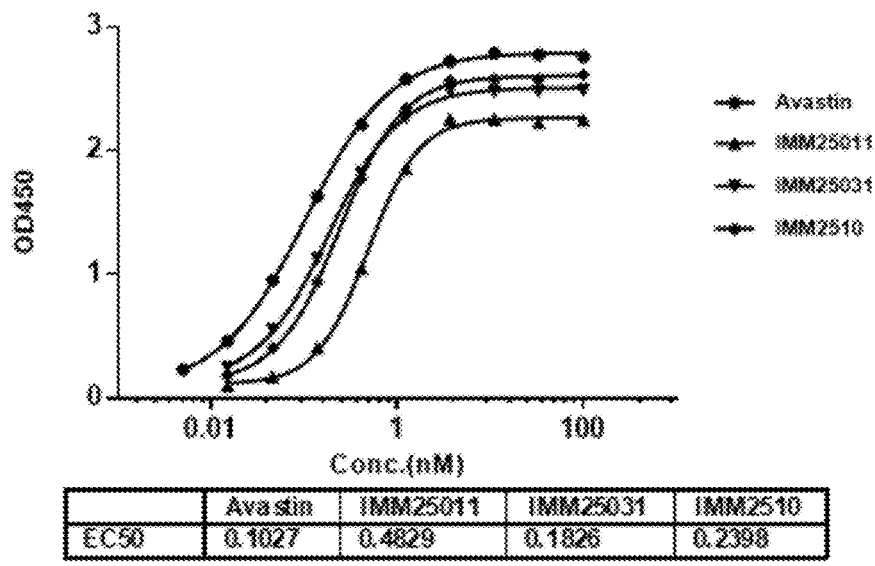
FIG. 3 shows binding activity of recombinant antibodies of the present disclosure to VEGF-165.

As shown in FIG. 3, the three recombinant antibodies of the present disclosure had similar binding activities to VAGF-165 but relatively 2 to 4 folds lower than that of Avastin.

Example 4

Recombinant Antibodies Bound to PD-L1

For PD-L1 binding analysis, 100 µl of $1 \times 10^6$/ml CHO-PD-L1 cells (ImmuneOnco, Cat #YMAK-0006) were incubated with 100 µl of serially titrated recombinant antibodies as well as control antibodies (Atezolizumab and Herceptin) at 4° C. for 40 minutes. After washed with cold PBS, cells were incubated with FITC-conjugated anti-human IgG-Fc antibody (Sigma, Cat #F9512). Then, the cells were washed for two times and subjected to FACS analysis.

Figure 4:
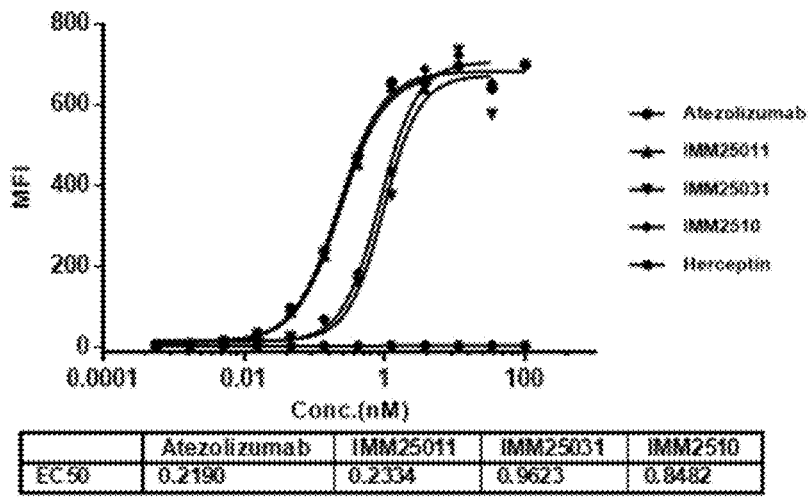
FIG. 4 shows binding activity of recombinant antibodies of the present disclosure to PD-L1.

The results as shown in FIG. 4 revealed that IMM25011, as expected due to its structure, had identical binding activity to that of Atezolizumab ($EC_{50}$=0.22 nM for Atezolizumab, $EC_{50}$=0.23 nM for IMM25011), while IMM25031

($EC_{50}$=0.96 nM) and IMM2510 (0.85 nM) had similar binding activities but relatively 4 folds lower than that of Atezolizumab.

Example 5

Recombinant Antibodies Bound to VEGF-165 and PD-L1 Simultaneously

For analysis of simultaneous binding activity of the recombinant antibodies to two targets, 100 µl of $1\times10^6$/ml CHO-PD-L1 cells (ImmuneOnco, Cat #YMAK-0006) were incubated with 100 µl of serially diluted IMM2510 for 45 minutes at 4° C. Cells were washed with cold PBS for two times, then incubated with 100 µl 40 nM biotin-conjugated VEGF-165 (Cat #11066-HNAH, Sino Biologicals) for 45 minutes at 4° C. After being washed for two times, cells were stained with FITC-conjugated Streptavidin (BD Pharmingen, Cat #554060, Lot #6169673) for another 45 minutes at 4° C. After washes, cells were subject to FACS analysis.

Figure 5:
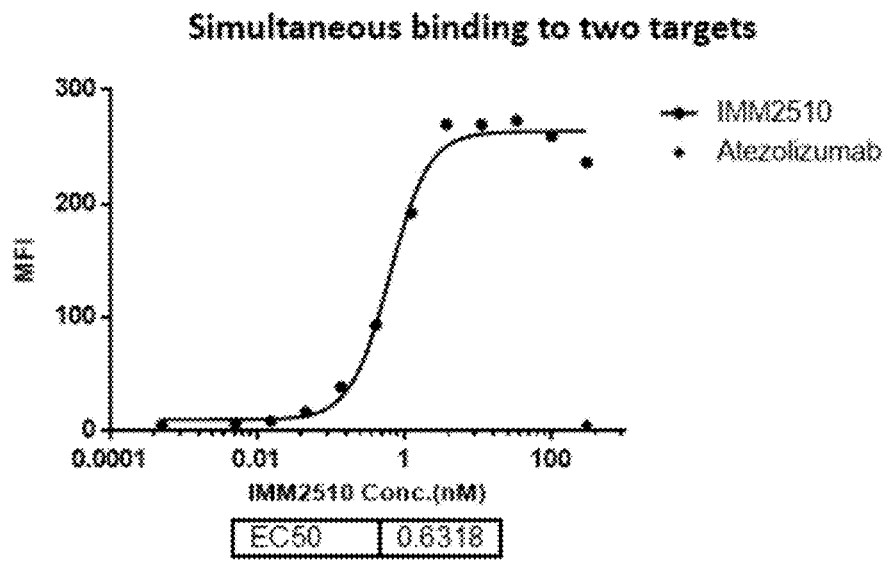
FIG. 5 shows simultaneous binding activity of recombinant antibodies of the present disclosure to VEGF-165 and PD-L1.

As shown in FIG. 5, with the increase of IMM2510 concentration, a dose-dependent increase in fluorescence signal was observed, suggesting a simultaneous binding of the two targets. The binding affinity of IMM2510 ($EC_{50}$=0.63 nM) was similar to that seen in single target-binding assay with PD-L1 ($EC_{50}$=0.85 nM).

Example 6

Recombinant Antibodies Induced Antibody-Dependent Cell-Mediated Cytotoxicity (ADCC)

CFSE-labeled Raji-PD-L1 cells (ImmuneOnco, Cat #YMAK-0007) as target cells, $6\times10^5$/ml, 50 were mixed with 100 µl of $6\times10^5$/ml NK92MI cells (ATCC, Cat #CRL-2408) as effector cells stably expressing FcγRIIIa at a 1:2 ratio, and the mixed cells were cultured for 4 hours at 37° C. under 5% $CO_2$ in the presence of 50 µl serially diluted IMM2510 or IMM25. Then propidium iodide (PI) (Sigma, Cat #P4170) was added to the cell culture at a concentration of 5 µg/ml, and the cell culture was subjected to FACS analysis for PI signals.

To confirm that ADCC activity would not be impacted by VEGF binding, VEGF-165 protein (Cat #11066-HNAH, Sino Biologicals) at a low (25 ng/ml) or high concentration (250 ng/ml) was added respectively together with IMM2510 or control antibodies to the cell culture, ADCC was analyzed following the procedure as described above.

Percentage of cell lysis caused by ADCC was calculated based on the following formula: % Lysis (or % ADCC)=(% PI Positive Cells with IMM2510 or IMM25−% PI Positive Cells with negative control protein)/(100−PI Positive Cells with negative control protein)*100.

Figure 6:
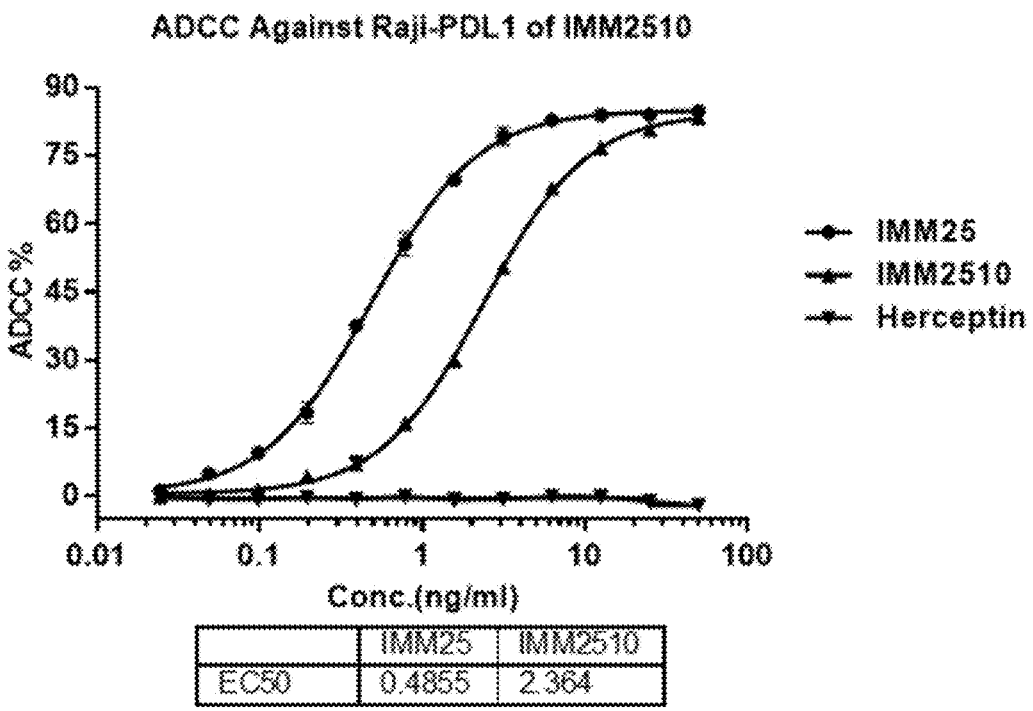
FIG. 6 shows IMM2510's ADCC activity against Raji-PD-L1.
Figure 7:
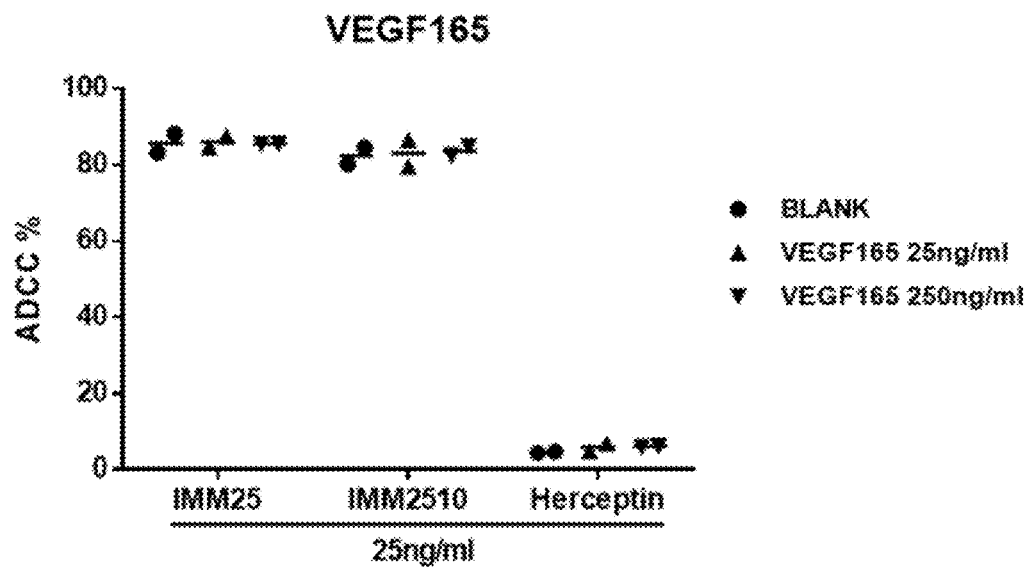
FIG. 7 shows IMM2510's ADCC activity against Raji-PD-L1 in the presence of VEGF-165.

The ADCC activity of IMM2510 showed a six folds decrease when compared to that of IMM25, as shown in FIG. 6, which might be due to the relatively lower PD-L1-binding affinity ($EC_{50}$=0.85 nM vs. $EC_{50}$=0.22 nM for IMM25). ADCC activity of IMM2510 was not impacted when VEGF-165 was added to the assay, as shown in FIG. 7, further suggesting a simultaneous but respective binding of the two targets.

Example 7

IMM2510 Had Good Anti-Tumor Effect

In vivo efficacy was evaluated using B-hPD-1 humanized mice (BIOCYTOGEN). Mouse colon cancer cells (MC-38) stably expressing human PD-L1 (MC38-PD-L1, BIOCYTOGEN) were prepared in serum-free medium and subcutaneously injected into the right flank of the B-hPD-1 humanized mice at the age of 6-8 weeks. When the tumor volume reached 100-200 $mm^3$, mice were randomly assigned into five groups with 6 mice in each group. Mice were treated respectively with PBS, IMM25 (5.0 mg/kg), VEGFR1-Fc (2.0 mg/kg), IMM2510 (6.0 mg/kg), and combination of IMM25 (5.0 mg/kg) and VEGFR1-Fc (2.0 mg/kg). Treatment was conducted intraperitoneally, twice a week for four weeks. Tumor volume and body weight were measured twice a week.

The tumor volume (V) was calculated as (length×$width^2$)/2. Tumor growth inhibition rate (TGI) was calculated by the formula: Tumor growth inhibition rate=(1−tumor volume change in administration group/tumor volume change in control group)×100%.

Results were expressed as mean±S.E.M. Comparisons between two groups were made by Dunnett's multi-comparison test, wherein P<0.05 was considered significant.

TABLE 1

Anti-tumor effect of IMM2510 and other agents

| Group | Drug | Animal# | Dose (mg/kg) | Treatment | TGI* |
|---|---|---|---|---|---|
| 1 | PBS | 6 | N/A | i.p, b.i.w. × 4 | |
| 2 | IMM25 | 6 | 5.0 | i.p, b.i.w. × 4 | 27.15% |
| 3 | VEGFR1-Fc | 6 | 2.0 | i.p, b.i.w. × 4 | 30.02% |
| 4 | IMM2510 | 6 | 6.0 | i.p, b.i.w. × 4 | 79.01% |
| 5 | IMM25 + VEGFR1-Fc | 6 | 5.0 + 2.0 | i.p, b.i.w. × 4 | 48.99% |

Figure 8:
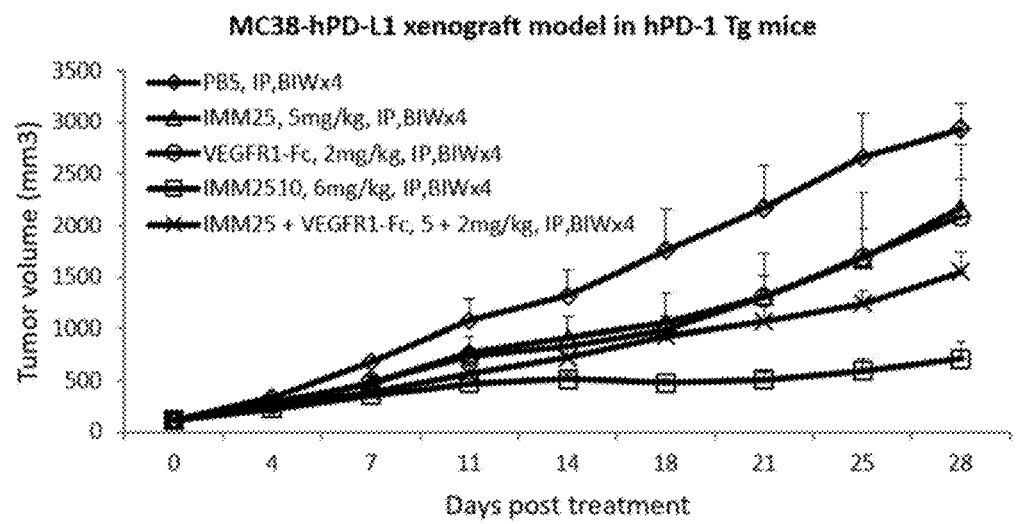
FIG. 8 shows in vivo therapeutic efficacy of IMM2505 in MC38-hPD-L1 xenograft model.

Tumor volume and TGI can be found in Table 1 and FIG. 8. Data showed that the tumor volume of the single agent-treated mice grew relatively slowly (mean tumor volume at day 28: IMM25=2168.0 $mm^3$, VEGFR1-Fc=2088.0 $mm^3$) compared to PBS (Mean value=2934.0 $mm^3$), while the tumor volume of mice treated with combination of the two single agents grew significantly more slowly (Mean value=1552.0 $mm^3$) than that treated with single agent. The recombinant antibody IMM2510 inhibited tumor growth with much stronger efficacy (Mean value=706.0 $mm^3$), even significantly better than the combination treatment.

Comparative Example 1

IMM0404's Anti-Tumor Activity in HT-29 or NCI-H1975 Xenograft Model

IMM0404 in this Example is a recombinant antibody, containing two SIRPαD1s each linked via a GS-linker, to an anti-EGFR antibody, Eribitux, at the N-terminus of each heavy chain. The SIRPαD1-GS-linker-anti-EGFR heavy chain has an amino acid sequence of SEQ ID NO: 23. The light chain of the anti-EGFR antibody has an amino acid sequence of SEQ ID NO: 24.

SIRPαD1-Fc is a fusion protein consisting of SIRPαD1 linked to an Fc fragment, which was described in WO2016169261. The amino acid sequence of this fusion protein is set forth in SEQ ID NO: 25.

HT-29 Xenograft Model

HT-29 human colon cancer cells were cultured in the McCoy's 5A medium containing 10% FBS at 37° C. and 5% $CO_2$. Cells at the logarithmic phase were collected and re-suspended in 1×PBS. The suspension was added with and mixed with Matrige at a volume ratio of 1:1, and the mixture contained 3×10⁷ cells per mL.

Forty mice were injected subcutaneously with HT-29 cells, 3×10⁶ cells per mouse, at the right flank. When tumor volume reached 100-200 mm³, these animals were randomly allocated into 5 groups with 8 mice in each group. Mice were respectively treated, once per week, through intraperitoneal injection with PBS, SIRPαD1-Fc (1.2 mg/kg), Erbitux (2.0 mg/kg), IMM0404 (2.7 mg/kg), and SIRPαD1-Fc+Erbitux (1.2 mg/kg+2.0 mg/kg), for 4 weeks. Totally four treatments were given. The day upon first dosing was defined as Day 0. Tumor volume and body weight were measured twice a week.

The tumor volume (V) was calculated as (length×width²)/2. Tumor growth inhibition rate (TGI) was calculated by the formula: Tumor growth inhibition rate=(1−tumor volume change in administration group/tumor volume change in control group)×100%. The student test was used to calculate group differences.

TABLE 2

Anti-tumor effect of IMM0404 and other antibodies

| Group | Drug | Animal# | Dose (mg/kg) | Treatment | TGI* |
|---|---|---|---|---|---|
| 1 | PBS | 8 | N/A | i.p, q.w. × 4 | |
| 2 | SIRPαD1-Fc | 8 | 1.2 | i.p, q.w. × 4 | 32.79% |
| 3 | Erbitux | 8 | 2.0 | i.p, q.w. × 4 | 40.00% |
| 4 | IMM0404 | 8 | 2.7 | i.p, q.w. × 4 | 18.48% |
| 5 | SIRPαD1-Fc + Erbitux | 8 | 1.2 + 2.0 | i.p, q.w. × 4 | 33.04% |

It can be seen from Table 2 that IMM0404 did not show better anti-tumor activity than other proteins in this xenograft model.

NCI-H1975 Xenograft Model

NCI-H1975 non-small cell lung cancer cells were cultured in the RPMI-1640 medium containing 10% FBS (GIBCO, US) at 37° C. and 5% CO₂. Cells at the logarithmic phase were collected and re-suspended in 1×PBS, 1×10⁷ cells per mL.

Forty SCID mice were injected subcutaneously with NCI-H1975 cells, 1×10⁶ cells per mouse, at the right flank. When tumor volume reached 100-200 mm³, these animals were randomly allocated into 5 groups with 8 mice in each group. Mice were respectively treated, once per week, through intraperitoneal injection with PBS, SIRPαD1-Fc (2.7 mg/kg), Erbitux (5.0 mg/kg), IMM0404 (6.0 mg/kg), and SIRPαD1-Fc+Erbitux (2.7 mg/kg+5.0 mg/kg), for 3 weeks. Totally three treatments were given. The day upon first dosing was defined as Day 0. Tumor volume and body weight were measured twice a week.

The tumor volume (V) was calculated as (length×width²)/2. Tumor growth inhibition rate (TGI) was calculated by the formula: Tumor growth inhibition rate=(1−tumor volume change in administration group/tumor volume change in control group)×100%. The student test was used to calculate group differences.

TABLE 3

Anti-tumor effect of IMM0404 and other antibodies

| Group | Drug | Animal# | Dose (mg/kg) | Treatment | TGI* |
|---|---|---|---|---|---|
| 1 | PBS | 8 | N/A | i.p, q.w. × 3 | |
| 2 | SIRPαD1-Fc | 8 | 2.7 | i.p, q.w. × 3 | 49.49% |
| 3 | Erbitux | 8 | 5.0 | i.p, q.w. × 3 | 85.69% |
| 4 | IMM0404 | 8 | 6.0 | i.p, q.w. × 3 | 68.77% |
| 5 | SIRPαD1-Fc + Erbitux | 8 | 2.7 + 5.0 | i.p, q.w. × 3 | 76.03% |

It can be seen from Table 3 that IMM0404's anti-tumor activity was better than SIRPαD1-Fc, but interior to Eribitux and SIRPαD1-Fc+Eribitux.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Several important amino acid sequences of the disclosure are listed below.

```
SEQ ID NO./Description/Sequence

SEQ ID NO.: 14
VEGFR1D2-linker-anti-PD-L1 heavy chain (IMM2510)
SDTGRPFVEMYSEIPEIIHMTEGRELVIPCRVTSPNITVTLKKFPLDT
LIPDGKRIIWDSRKGFIISAATYKEIGLLTCEATVNGHLYKTNYLTHR
QTNTGGGGSGGGGSGGGGSEVQLVESGGGLVQPGGSLRLSCAASGFTF
SDSWIHWVRQAPGKGLEWVAWISPYGGSTYYADSVKGRFTISADTSKN
TAYLQMNSLRAEDTAVYYCARRHWPGGFDYWGQGTLVTVSSASTKGPS
VFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSH
EDPEVKFNWYVDGVEVHNAKTKPREEQYNATYRVVSVLTVLHQDWLNG
KEYKCKVSNKALPAPIAATISKAKGQPREPQVYTLPPSREEMTKNQVS
LTCLVKGFYPSDIAVEWESNGQPENNYKTTPPVLDSDGSFFLYSKLTV
DKSRWQQGNVFSCSVMHEALHNHYTQKSLSLSPG SEQ ID NO.: 16
anti-PD-L1 heavy chain-Linker-
VEGFR1D2 (IMM25011)
EVQLVESGGGLVQPGGSLRLSCAASGFTFSDSWIHWVRQAPGKGLEWV
AWISPYGGSTYYADSVKGRFTISADTSKNTAYLQMNSLRAEDTAVYYC
ARRHWPGGFDYWGQGTLVTVSSASTKGPSVFPLAPSSKSTSGGTAALG
CLVKDYFPEPVTVSWNSGALTSGVHTFPAVLQSSGLYSLSSVVTVPSS
SLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEA
LHNHYTQKSLSLSPGGGGGSGGGGSSDTGRPFVEMYSEIPEIIHMTEG
RELVIPCRVTSPNITVTLKKFPLDTLIPDGKRIIWDSRKGFIISAATY
KEIGLLTCEATVNGHLYKTNYLTHRQTNT SEQ ID NO.: 6
Light chain of IMM2510, IMM25011 and IMM25
DIQMTQSPSSLSASVGDRVTITCRASQDVSTAVAWYQQKPGKAPKLLI
YSASFLYSGVPSRFSGSGSGTDFTLTISSLQPEDFATYYCQQYLYHPA
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC SEQ ID NO.: 18
VEGFR1D2-linker-anti-PD-L1 light
chain (IMM25031)
SDTGRPFVEMYSEIPEIIHMTEGRELVIPCRVTSPNITVTLKKFPLDT
LIPDGKRIIWDSRKGFIISAATYKEIGLLTCEATVNGHLYKTNYLTHR
QTNTGGGGSGGGGSGGGGSDIQMTQSPSSLSASVGDRVTITCRASQDV
STAVAWYQQKPGKAPKLLIYSASFLYSGVPSRFSGSGSGTDFTLTISS
LQPEDFATYYCQQYLYHPATFGQGTKVEIKRTVAAPSVFIFPPSDEQL
KSGTASVVCLLNNFYPREAKVQWKVDNALQSGNSQESVTEQDSKDSTY
SLSSTLTLSKADYEKHKVYACEVTHQGLSSPVTKSFNRGEC
```

| SEQ ID NO./Description/Sequence |
| --- |
| SEQ ID NO.: 2<br>Heavy chain of IMM25031 and IMM25<br>EVQLVESGGGLVQPGGSLRLSCAASGFTFSDSWIHWVRQAPGKGLEWV<br>AWISPYGGSTYYADSVKGRFTISADTSKNTAYLQMNSLRAEDTAVYYC<br>ARRHWPGGFDYWGQGTLVTVSSASTKGPSVFPLAPSSKSTSGGTAALG<br>CLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLGGPS |

| SEQ ID NO./Description/Sequence |
| --- |
| VFLFPPKPKDTLMISRTPEVTCVVVDVSHEDPEVKFNWYVDGVEVHNA<br>KTKPREEQYNATYRVVSVLTVLHQDWLNGKEYKCKVSNKALPAPIAAT<br>ISKAKGQPREPQVYTLPPSREEMTKNQVSLTCLVKGFYPSDIAVEWES<br>NGQPENNYKTTPPVLDSDGSFFLYSKLTVDKSRWQQGNVFSCSVMHEA<br>LHNHYTQKSLSLSPGK |

We claim:

1. A recombinant protein, comprising
   an anti-PD-L1 antibody comprising a heavy chain and a light chain, and
   an extracellular Ig-like domain of a vascular epithelial growth factor receptor (VEGFR), linked via a linker to N-terminus of the heavy chain,
   wherein the heavy chain comprises SEQ ID NO: 2, and the light chain SEQ ID NO: 6,
   wherein the extracellular Ig-like domain of VEGFR is a second extracellular Ig-like domain of VEGFR1 and comprises SEQ ID NO: 8,
   wherein the linker comprises SEQ ID NO: 12, and
   wherein the recombinant protein is capable of binding PD-L1, VEGF and Fc receptor simultaneously.

2. The recombinant protein according to claim 1, wherein the anti-PD-L1 antibody is Atezolizumab.

3. The recombinant protein according to claim 1, wherein the heavy chain with the extracellular Ig-like domain of VEGFR comprises SEQ ID NO.:14.

4. A polynucleotide encoding the recombinant protein according to claim 1.

5. A vector containing the polynucleotide according to claim 4.

6. A host cell containing the vector according to claim 5.

7. A pharmaceutical composition, comprising the recombinant protein according to claim 1, and a pharmaceutically acceptable carrier.

8. A method for treating a disease caused by overexpression of VEGF or PD-L1, or both, selected from group consisting of breast cancer, lung cancer and colon cancer, comprising administering to a patient or a subject in need thereof a therapeutically effective amount of the pharmaceutical composition of claim 7.

* * * * *

UNITED STATES PATENT AND TRADEMARK OFFICE
CERTIFICATE OF CORRECTION

| | | |
|---|---|---|
| PATENT NO. | : 11,407,832 B2 | Page 1 of 1 |
| APPLICATION NO. | : 16/699732 | |
| DATED | : August 9, 2022 | |
| INVENTOR(S) | : Wenzhi Tian | |

It is certified that error appears in the above-identified patent and that said Letters Patent is hereby corrected as shown below:

On the Title Page

Item [71] should read as:
Immuneonco Biopharmaceuticals (Shanghai) Inc., Shanghai (CN)

Signed and Sealed this
Fifteenth Day of November, 2022

Katherine Kelly Vidal
*Director of the United States Patent and Trademark Office*

SEQUENCE LISTING

<160> NUMBER OF SEQ ID NOS: 25

<210> SEQ ID NO 1
<211> LENGTH: 1347
<212> TYPE: DNA
<213> ORGANISM: Artificial Sequence
<220> FEATURE:
<223> OTHER INFORMATION: nucleotide sequence of heavy chain of anti-PD-
      L1 antibody

<400> SEQUENCE: 1

```
gaggtgcagc tggtcgagtc tggcggcggc ctcgttcaac caggcgggag cctgcggctc        60
agctgcgccg catctggatt cacctttct gattcttgga tccactgggt tcgccaggcc       120
cctggaaagg gactggagtg ggttgcctgg atctccccat atggtggctc gacttattat       180
gccgactctg tgaaaggacg gtttactatc tccgcggaca ctagcaaaaa taccgcatac       240
ctgcagatga actctctccg cgctgaagat acagctgtgt actactgcgc aagacgtcac       300
tggcccggcg gattcgacta ttgggggcag ggcactctgg tcaccgtgtc ctccgctagc       360
accaagggcc catcggtctt ccccctggca ccctcctcca agagcacctc tgggggcaca       420 gcggcctgg gctgcctggt caaggactac ttccccgaac cggtgacggt gtcgtggaac       480
tcaggcgccc tgaccagcgg cgtgcacacc ttccggctg cctacagtc ctcaggactc        540 tactccctca gcagcgtggt gaccgtgccc tccagcagct gggcaccca gacctacatc       600 tgcaacgtga atcacaagcc cagcaacacc aaggtggaca gagagttga gcccaaatct       660 tgtgacaaaa ctcacacatg cccaccgtgc ccagcacctg aactcctggg ggaccgtca       720 gtcttcctct tccccccaaa acccaaggac accctcatga tctcccggac ccctgaggtc       780
acatgcgtgg tggtggacgt gagccacgaa gaccctgagg tcaagttcaa ctggtatgtg       840
gacggcgtgg aggtgcataa tgccaagaca aagccgcggg aggagcagta caacgccacg       900
taccgtgtgg tcagcgtcct caccgtcctg caccagact ggctgaatgg caaggagtac       960
aagtgcaagg tctccaacaa agccctccca gcccccatcg ccgcaaccat ctccaaagcc      1020
aaagggcagc ccgagaacc acaggtgtac accctgcccc catcccggga ggagatgacc      1080
aagaaccaag tcagcctgac ctgcctggtc aaaggcttct atcccagcga catcgccgtg      1140
gagtgggaga gcaatgggca gccggagaac aactacaaga ccacgcctcc cgtgctggac      1200
tccgacggct ccttcttcct ctattccaag ctcaccgtgg acaagagcag gtggcagcag      1260
gggaacgtct tctcatgctc cgtgatgcat gaggctctgc acaaccacta cacgcagaag      1320
agcctctccc tgtctccggg caaatga                                          1347
```

<210> SEQ ID NO 2
<211> LENGTH: 448
<212> TYPE: PRT
<213> ORGANISM: Artificial Sequence
<220> FEATURE:

<223> OTHER INFORMATION: amino acid sequence of heavy chain of anti-PD-L1 antibody

<400> SEQUENCE: 2

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Asp Ser
             20                  25                  30
Trp Ile His Trp Val Arg Gln Ala Pro Gly Lys Gly Leu Glu Trp Val
         35                  40                  45
Ala Trp Ile Ser Pro Tyr Gly Gly Ser Thr Tyr Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Arg His Trp Pro Gly Gly Phe Asp Tyr Trp Gly Gln Gly Thr
             100                 105                 110
Leu Val Thr Val Ser Ser Ala Ser Thr Lys Gly Pro Ser Val Phe Pro
         115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ala Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Ala Ala Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
```

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 3
<211> LENGTH: 1344
<212> TYPE: DNA
<213> ORGANISM: Artificial Sequence
<220> FEATURE:
<223> OTHER INFORMATION: nucleotide sequence of heavy chain of anti-PD-
      L1 antibody

<400> SEQUENCE: 3

```
gaggtgcagc tggtcgagtc tggcggcggc ctcgttcaac caggcgggag cctgcggctc    60
agctgcgccg catctggatt cacctttcct gattcttgga tccactgggt tcgccaggcc   120
cctggaaagg gactggagtg ggttgcctgg atctccccat atggtggctc gacttattat   180
gccgactctg tgaaaggacg gtttactatc tccgcggaca ctagcaaaaa taccgcatac   240
ctgcagatga actctctccg cgctgaagat acagctgtgt actactgcgc aagacgtcac   300
tggcccggcg gattcgacta ttgggggcag ggcactctgg tcaccgtgtc ctccgctagc   360
accaagggcc catcggtctt ccccctggca ccctcctcca gagcacctc tgggggcaca    420 gcggccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct gggcaccca gacctacatc    600 tgcaacgtga atcacaagcc cagcaacacc aaggtggaca gagagttga gcccaaatct    660 tgtgacaaaa ctcacacatg cccaccgtgc ccagcacctg aactcctggg gggaccgtca   720
gtcttcctct tccccccaaa acccaaggac accctcatga tctcccggac ccctgaggtc   780
acatgcgtgg tggtggacgt gagccacgaa gaccctgagg tcaagttcaa ctggtatgtg   840
gacggcgtgg aggtgcataa tgccaagaca aagccgcggg aggagcagta caacgccacg   900
taccgtgtgg tcagcgtcct caccgtcctg caccaagact ggctgaatgg caaggagtac   960
aagtgcaagg tctccaacaa agccctccca gcccccatcg ccgcaaccat ctccaaagcc  1020
aaagggcagc cccgagaacc acaggtgtac accctgcccc catcccggga ggagatgacc  1080
aagaaccaag tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctattccaag ctcaccgtgg acaagagcag gtggcagcag  1260
gggaacgtct tctcatgctc cgtgatgcat gaggctctgc acaaccacta cacgcagaag  1320
agcctctccc tgtctccggg ctga                                         1344
```

<210> SEQ ID NO 4
<211> LENGTH: 447
<212> TYPE: PRT
<213> ORGANISM: Artificial Sequence
<220> FEATURE:
<223> OTHER INFORMATION: amino acid sequence of heavy chain of anti-PD-
      L1 antibody

<400> SEQUENCE: 4

Glu Val Gln Leu Val Glu Ser Gly Gly Gly Leu Val Gln Pro Gly Gly

```
1               5                   10                  15
Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
                35                  40                  45

Ala Trp Ile Ser Pro Tyr Gly Gly Ser Thr Tyr Tyr Ala Asp Ser Val
                50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ala Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Ala Ala Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430
```

Leu His Asn His Tyr Thr Gln Lys Ser Leu Ser Leu Ser Pro Gly
            435                 440                 445

<210> SEQ ID NO 5
<211> LENGTH: 645
<212> TYPE: DNA
<213> ORGANISM: Artificial Sequence
<220> FEATURE:
<223> OTHER INFORMATION: nucleotide sequence of light chain of anti-PD-
      L1 antibody

<400> SEQUENCE: 5

```
gatattcaaa tgacacaaag cccttcttcc ctgagcgctt ctgtgggcga ccgcgttaca    60
atcacatgca gggcaagcca ggatgtcagc actgctgtcg cttggtacca gcagaaacca   120
ggcaaggcac ctaagctcct gatctactcc gcctccttcc tgtattccgg agtcccctcc   180
cgcttttccg gctccgggtc tgggaccgat ttcaccctga ccatcagctc cctccagcct   240
gaagattttg ccacctatta ttgtcagcag tacctctatc acccagcgac ctttgggcag   300
gggacaaaag tggagatcaa gcgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 6
<211> LENGTH: 214
<212> TYPE: PRT
<213> ORGANISM: Artificial Sequence
<220> FEATURE:
<223> OTHER INFORMATION: amino acid sequence of light chain of anti-PD-
      L1 antibody

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser

```
                    165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 300
<212> TYPE: DNA
<213> ORGANISM: Artificial Sequence
<220> FEATURE:
<223> OTHER INFORMATION: Nucleotide sequence of VEGFR1D2

<400> SEQUENCE: 7
agtgatacag gtagaccttt cgtagagatg tacagtgaaa tccccgaaat tatacacatg      60
actgaaggaa gggagctcgt cattccctgc cgggttacgt cacctaacat cactgttact     120
ttaaaaaagt ttccacttga cactttgatc cctgatggaa aacgcataat ctgggacagt     180
agaaagggct tcatcatatc agctgcaacg tacaaagaaa tagggcttct gacctgtgaa     240
gcaacagtca atgggcattt gtataagaca aactatctca cacatcgaca aaccaataca     300

<210> SEQ ID NO 8
<211> LENGTH: 100
<212> TYPE: PRT
<213> ORGANISM: Artificial Sequence
<220> FEATURE:
<223> OTHER INFORMATION: amino acid sequence of VEGFR1D2

<400> SEQUENCE: 8

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Ala Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr
        100

<210> SEQ ID NO 9
<211> LENGTH: 30
<212> TYPE: DNA
<213> ORGANISM: Artificial Sequence
<220> FEATURE:
<223> OTHER INFORMATION: nucleotide sequence of linker

<400> SEQUENCE: 9
ggcggcggtg ggagcggcgg cggtgggagc                                       30

<210> SEQ ID NO 10
<211> LENGTH: 10
<212> TYPE: PRT
<213> ORGANISM: Artificial Sequence
```

```
<220> FEATURE:
<223> OTHER INFORMATION: amino acid sequence of linker

<400> SEQUENCE: 10

Gly Gly Gly Gly Ser Gly Gly Gly Gly Ser
1               5                   10

<210> SEQ ID NO 11
<211> LENGTH: 45
<212> TYPE: DNA
<213> ORGANISM: Artificial Sequence
<220> FEATURE:
<223> OTHER INFORMATION: nucleotide sequence of linker

<400> SEQUENCE: 11
ggcggcggtg ggagcggcgg cggtgggagc ggcggcgggg gctcg            45

<210> SEQ ID NO 12
<211> LENGTH: 15
<212> TYPE: PRT
<213> ORGANISM: Artificial Sequence
<220> FEATURE:
<223> OTHER INFORMATION: amino acid sequence of linker

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 1689
<212> TYPE: DNA
<213> ORGANISM: Artificial Sequence
<220> FEATURE:
<223> OTHER INFORMATION: nucleotide sequence of heavy chain of IMM2510

<400> SEQUENCE: 13
agtgatacag gtagaccttt cgtagagatg tacagtgaaa tccccgaaat tatacacatg      60
actgaaggaa gggagctcgt cattccctgc cgggttacgt cacctaacat cactgttact     120 ttaaaaagt ttccacttga cactttgatc cctgatggaa acgcataat ctgggacagt       180 agaaagggct tcatcatatc agctgcaacg tacaaagaaa tagggcttct gacctgtgaa     240
gcaacagtca atgggcattt gtataagaca aactatctca cacatcgaca aaccaataca     300
ggcggcggtg ggagcggcgg cggtgggagc ggcggcgggg gctcggaggt gcagctggtc     360
gagtctggcg gcggcctcgt tcaaccaggc gggagcctgc ggctcagctg cgccgcatct     420
ggattcacct tttctgattc ttggatccac tgggttcgcc aggcccctgg aaagggactg     480
gagtgggttg cctggatctc cccatatggt ggctcgactt attatgccga ctctgtgaaa     540
ggacggttta ctatctccgc ggacactagc aaaaataccg catacctgca gatgaactct     600
ctccgcgctg aagatacagc tgtgtactac tgcgcaagac gtcactggcc ggcggattc      660 gactattggg gcagggcac tctggtcacc gtgtcctccg ctagcaccaa gggcccatcg     720
gtcttccccc tggcaccctc ctccaagagc acctctgggg gcacagcggc cctgggctgc     780
ctggtcaagg actacttccc cgaaccggtg acggtgtcgt ggaactcagg cgccctgacc     840
agcggcgtgc acaccttccc ggctgtccta cagtcctcag gactctactc cctcagcagc     900
gtggtgaccg tgccctccag cagcttgggc acccagacct acatctgcaa cgtgaatcac     960
aagcccagca acaccaaggt ggacaagaga gttgagccca atcttgtgac aaaaactcac    1020
acatgcccac cgtgcccagc acctgaactc ctggggggac cgtcagtctt cctcttcccc    1080
```

-continued

```
ccaaaaccca aggacaccct catgatctcc cggacccctg aggtcacatg cgtggtggtg   1140
gacgtgagcc acgaagaccc tgaggtcaag ttcaactggt atgtggacgg cgtggaggtg   1200
cataatgcca agacaaagcc gcgggaggag cagtacaacg ccacgtaccg tgtggtcagc   1260
gtcctcaccg tcctgcacca agactggctg aatggcaagg agtacaagtg caaggtctcc   1320
aacaaagccc tcccagcccc catcgccgca accatctcca aagccaaagg gcagcccga   1380 gaaccacagg tgtacaccct gcccccatcc cgggaggaga tgaccaagaa ccaagtcagc   1440
ctgacctgcc tggtcaaagg cttctatccc agcgacatcg ccgtggagtg ggagagcaat   1500
gggcagccgg agaacaacta caagaccacg cctcccgtgc tggactccga cggctccttc   1560
ttcctctatt ccaagctcac cgtggacaag agcaggtggc agcaggggaa cgtcttctca   1620
tgctccgtga tgcatgaggc tctgcacaac cactacacgc agaagagcct ctccctgtct   1680
ccgggctga                                                          1689
```

<210> SEQ ID NO 14
<211> LENGTH: 562
<212> TYPE: PRT
<213> ORGANISM: Artificial Sequence
<220> FEATURE:
<223> OTHER INFORMATION: amino acid sequence of heavy chain of IMM2510

<400> SEQUENCE: 14

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Ala Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Gly Gly Gly Ser Gly Gly Gly Ser Gly Gly
            100                 105                 110

Gly Gly Ser Glu Val Gln Leu Val Glu Ser Gly Gly Leu Val Gln
        115                 120                 125

Pro Gly Gly Ser Leu Arg Leu Ser Cys Ala Ala Ser Gly Phe Thr Phe
    130                 135                 140

Ser Asp Ser Trp Ile His Trp Val Arg Gln Ala Pro Gly Lys Gly Leu
145                 150                 155                 160

Glu Trp Val Ala Trp Ile Ser Pro Tyr Gly Ser Thr Tyr Tyr Ala
                165                 170                 175

Asp Ser Val Lys Gly Arg Phe Thr Ile Ser Ala Asp Thr Ser Lys Asn
            180                 185                 190

Thr Ala Tyr Leu Gln Met Asn Ser Leu Arg Ala Glu Asp Thr Ala Val
        195                 200                 205

Tyr Tyr Cys Ala Arg Arg His Trp Pro Gly Gly Phe Asp Tyr Trp Gly
    210                 215                 220

Gln Gly Thr Leu Val Thr Val Ser Ser Ala Ser Thr Lys Gly Pro Ser
225                 230                 235                 240

Val Phe Pro Leu Ala Pro Ser Ser Lys Ser Thr Ser Gly Gly Thr Ala
                245                 250                 255
```

Ala Leu Gly Cys Leu Val Lys Asp Tyr Phe Pro Glu Pro Val Thr Val
             260                 265                 270

Ser Trp Asn Ser Gly Ala Leu Thr Ser Gly Val His Thr Phe Pro Ala
             275                 280                 285

Val Leu Gln Ser Ser Gly Leu Tyr Ser Leu Ser Ser Val Val Thr Val
290                 295                 300

Pro Ser Ser Ser Leu Gly Thr Gln Thr Tyr Ile Cys Asn Val Asn His
305                 310                 315                 320

Lys Pro Ser Asn Thr Lys Val Asp Lys Arg Val Glu Pro Lys Ser Cys
             325                 330                 335

Asp Lys Thr His Thr Cys Pro Pro Cys Pro Ala Pro Glu Leu Leu Gly
             340                 345                 350

Gly Pro Ser Val Phe Leu Phe Pro Pro Lys Pro Lys Asp Thr Leu Met
             355                 360                 365

Ile Ser Arg Thr Pro Glu Val Thr Cys Val Val Val Asp Val Ser His
             370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ala Thr Tyr
             405                 410                 415

Arg Val Val Ser Val Leu Thr Val Leu His Gln Asp Trp Leu Asn Gly
             420                 425                 430

Lys Glu Tyr Lys Cys Lys Val Ser Asn Lys Ala Leu Pro Ala Pro Ile
             435                 440                 445

Ala Ala Thr Ile Ser Lys Ala Lys Gly Gln Pro Arg Glu Pro Gln Val
             450                 455                 460

Tyr Thr Leu Pro Pro Ser Arg Glu Glu Met Thr Lys Asn Gln Val Ser
465                 470                 475                 480

Leu Thr Cys Leu Val Lys Gly Phe Tyr Pro Ser Asp Ile Ala Val Glu
             485                 490                 495

Trp Glu Ser Asn Gly Gln Pro Glu Asn Asn Tyr Lys Thr Thr Pro Pro
             500                 505                 510

Val Leu Asp Ser Asp Gly Ser Phe Phe Leu Tyr Ser Lys Leu Thr Val
             515                 520                 525

Asp Lys Ser Arg Trp Gln Gln Gly Asn Val Phe Ser Cys Ser Val Met
             530                 535                 540

His Glu Ala Leu His Asn His Tyr Thr Gln Lys Ser Leu Ser Leu Ser
545                 550                 555                 560

Pro Gly

<210> SEQ ID NO 15
<211> LENGTH: 1674
<212> TYPE: DNA
<213> ORGANISM: Artificial Sequence
<220> FEATURE:
<223> OTHER INFORMATION: nucleotide sequence of heavy chain of IMM25011

<400> SEQUENCE: 15
gaggtgcagc tggtcgagtc tggcggcggc ctcgttcaac caggcgggag cctgcggctc        60
agctgcgccg catctggatt cacctttttct gattcttgga tccactgggt tcgccaggcc      120
cctggaaagg gactggagtg ggttgcctgg atctccccat atggtggctc gacttattat      180
gccgactctg tgaaaggacg gtttactatc tccgcggaca ctagcaaaaa taccgcatac      240
ctgcagatga actctctccg cgctgaagat acagctgtgt actactgcgc aagacgtcac      300

```
tggcccggcg gattcgacta ttgggggcag ggcactctgg tcaccgtgtc ctccgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc     600 tgcaacgtga atcacaagcc cagcaacacc aaggtggaca gagagttga gcccaaatct     660 tgtgacaaaa ctcacacatg cccaccgtgc ccagcacctg aactcctggg gggaccgtca    720
gtcttcctct ccccccaaa accccaaggac accctcatga tctcccggac ccctgaggtc    780
acatgcgtgg tggtggacgt gagccacgaa gaccctgagg tcaagttcaa ctggtatgtg    840
gacggcgtga aggtgcataa tgccaagaca agccgcgggg aggagcagta caactccacg    900
taccgtgtgg tcagcgtcct caccgtcctg caccaagact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga ggagatgacc   1080
aagaaccaag tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctattccaag ctcaccgtgg acaagagcag gtggcagcag   1260
gggaacgtct tctcatgctc cgtgatgcat gaggctctgc acaaccacta cacgcagaag   1320
agcctctccc tgtctccggg cggcggcggt gggagcggcg gcggtgggag cagtgataca   1380 ggtagaccctt tcgtagagat gtacagtgaa atccccgaaa ttatacacat gactgaagga   1440
agggagctcg tcattccctg ccgggttacg tcacctaaca tcactgttac tttaaaaaag   1500
tttccacttg acactttgat ccctgatgga aaacgcataa tctgggacag tagaaagggc   1560
ttcatcatat cagctgcaac gtacaaagaa atagggcttc tgacctgtga agcaacagtc   1620
aatgggcatt tgtataagac aaactatctc acacatcgac aaaccaatac atga          1674
```

<210> SEQ ID NO 16
<211> LENGTH: 557
<212> TYPE: PRT
<213> ORGANISM: Artificial Sequence
<220> FEATURE:
<223> OTHER INFORMATION: amino acid sequence of heavy chain of IMM25011

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro

```
            115                 120                 125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Gly
            435                 440                 445

Gly Gly Gly Ser Gly Gly Gly Gly Ser Ser Asp Thr Gly Arg Pro Phe
    450                 455                 460

Val Glu Met Tyr Ser Glu Ile Pro Glu Ile Ile His Met Thr Glu Gly
465                 470                 475                 480

Arg Glu Leu Val Ile Pro Cys Arg Val Thr Ser Pro Asn Ile Thr Val
                485                 490                 495

Thr Leu Lys Lys Phe Pro Leu Asp Thr Leu Ile Pro Asp Gly Lys Arg
                500                 505                 510

Ile Ile Trp Asp Ser Arg Lys Gly Phe Ile Ile Ser Ala Ala Thr Tyr
            515                 520                 525

Lys Glu Ile Gly Leu Leu Thr Cys Glu Ala Thr Val Asn Gly His Leu
    530                 535                 540
```

Tyr Lys Thr Asn Tyr Leu Thr His Arg Gln Thr Asn Thr
545                 550                 555

<210> SEQ ID NO 17
<211> LENGTH: 990
<212> TYPE: DNA
<213> ORGANISM: Artificial Sequence
<220> FEATURE:
<223> OTHER INFORMATION: nucleotide sequence of light chain of IMM25031

<400> SEQUENCE: 17
agtgatacag gtagaccttt cgtagagatg tacagtgaaa tccccgaaat tatacacatg      60
actgaaggaa gggagctcgt cattccctgc cgggttacgt cacctaacat cactgttact     120
ttaaaaaagt ttccacttga cactttgatc cctgatggaa aacgcataat ctgggacagt     180
agaaagggct tcatcatatc agctgcaacg tacaaagaaa tagggcttct gacctgtgaa     240
gcaacagtca atgggcattt gtataagaca aactatctca cacatcgaca aaccaataca     300
ggcggcggtg ggagcggcgg cggtgggagc ggcggcgggg gctcggatat tcaaatgaca     360
caaagccctt cttccctgag cgcttctgtg ggcgaccgcg ttacaatcac atgcagggca     420
agccaggatg tcagcactgc tgtcgcttgg taccagcaga accaggcaa ggcacctaag     480 ctcctgatct actccgcctc cttcctgtat tccggagtcc cctcccgctt tccggctcc      540 gggtctggga ccgatttcac cctgaccatc agctccctcc agcctgaaga ttttgccacc     600
tattattgtc agcagtacct ctatcaccca gcgacctttg gcaggggac aaaagtggag      660 atcaagcgaa ctgtggctgc accatctgtc ttcatcttcc cgccatctga tgagcagttg     720
aaatctggaa ctgcctctgt tgtgtgcctg ctgaataact tctatcccag agaggccaaa     780
gtacagtgga aggtggataa cgccctccaa tcgggtaact cccaggagag tgtcacagag     840
caggacagca aggacagcac ctacagcctc agcagcaccc tgacgctgag caaagcagac     900
tacgagaaac acaaagtcta cgcctgcgaa gtcaccccat cagggcctgag ctcgcccgtc    960 acaaagagct tcaacagggg agagtgttag                                     990

<210> SEQ ID NO 18
<211> LENGTH: 329
<212> TYPE: PRT
<213> ORGANISM: Artificial Sequence
<220> FEATURE:
<223> OTHER INFORMATION: amino acid sequence of light chain of IMM25031

<400> SEQUENCE: 18

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Ala Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Gly Gly Gly Gly Ser Gly Gly Gly Ser Gly Gly
            100                 105                 110

```
Gly Gly Ser Asp Ile Gln Met Thr Gln Ser Pro Ser Ser Leu Ser Ala
            115                 120                 125

Ser Val Gly Asp Arg Val Thr Ile Thr Cys Arg Ala Ser Gln Asp Val
        130                 135                 140

Ser Thr Ala Val Ala Trp Tyr Gln Gln Lys Pro Gly Lys Ala Pro Lys
145                 150                 155                 160

Leu Leu Ile Tyr Ser Ala Ser Phe Leu Tyr Ser Gly Val Pro Ser Arg
                165                 170                 175

Phe Ser Gly Ser Gly Ser Gly Thr Asp Phe Thr Leu Thr Ile Ser Ser
            180                 185                 190

Leu Gln Pro Glu Asp Phe Ala Thr Tyr Tyr Cys Gln Gln Tyr Leu Tyr
        195                 200                 205

His Pro Ala Thr Phe Gly Gln Gly Thr Lys Val Glu Ile Lys Arg Thr
        210                 215                 220

Val Ala Ala Pro Ser Val Phe Ile Phe Pro Pro Ser Asp Glu Gln Leu
225                 230                 235                 240

Lys Ser Gly Thr Ala Ser Val Val Cys Leu Leu Asn Asn Phe Tyr Pro
                245                 250                 255

Arg Glu Ala Lys Val Gln Trp Lys Val Asp Asn Ala Leu Gln Ser Gly
            260                 265                 270

Asn Ser Gln Glu Ser Val Thr Glu Gln Asp Ser Lys Asp Ser Thr Tyr
        275                 280                 285

Ser Leu Ser Ser Thr Leu Thr Leu Ser Lys Ala Asp Tyr Glu Lys His
        290                 295                 300

Lys Val Tyr Ala Cys Glu Val Thr His Gln Gly Leu Ser Ser Pro Val
305                 310                 315                 320

Thr Lys Ser Phe Asn Arg Gly Glu Cys
                325

<210> SEQ ID NO 19
<211> LENGTH: 57
<212> TYPE: DNA
<213> ORGANISM: Artificial Sequence
<220> FEATURE:
<223> OTHER INFORMATION: nucleotide sequence of signal peptide of mouse
      IgG1 heavy chain

<400> SEQUENCE: 19
atgggatggt catgtatcat ccttttttctg gtagcaactg caactggagt acattca        57

<210> SEQ ID NO 20
<211> LENGTH: 9
<212> TYPE: DNA
<213> ORGANISM: Artificial Sequence
<220> FEATURE:
<223> OTHER INFORMATION: Kozak sequence

<400> SEQUENCE: 20 gccgccacc                                                              9

<210> SEQ ID NO 21
<211> LENGTH: 1005
<212> TYPE: DNA
<213> ORGANISM: Artificial Sequence
<220> FEATURE:
<223> OTHER INFORMATION: nucleotide sequence of VEGFR1-Fc

<400> SEQUENCE: 21
agtgatacag gtagaccttt cgtagagatg tacagtgaaa tccccgaaat tatacacatg      60
```

-continued

```
actgaaggaa gggagctcgt cattccctgc cgggttacgt cacctaacat cactgttact    120
ttaaaaaagt ttccacttga cactttgatc cctgatggaa aacgcataat ctgggacagt    180
agaaagggct tcatcatatc agctgcaacg tacaaagaaa tagggcttct gacctgtgaa    240
gcaacagtca atgggcattt gtataagaca aactatctca cacatcgaca aaccaataca    300
gaattcgagc ccaaatcttg tgacaaaact cacacatgcc caccgtgccc agcacctgaa    360
ctcctggggg gaccgtcagt cttcctcttc cccccaaaac ccaaggacac cctcatgatc    420
tcccggaccc ctgaggtcac atgcgtggtg gtggacgtga gccacgaaga ccctgaggtc    480
aagttcaact ggtacgtgga cggcgtggag gtgcataatg ccaagacaaa gccgcgggag    540
gagcagtaca acagcacgta ccgtgtggtc agcgtcctca ccgtcctgca ccaggactgg    600
ctgaatggca aggagtacaa gtgcaaggtc tccaacaaag ccctcccagc ccccatcgag    660
aaaaccatct ccaaagccaa agggcagccc cgagaaccac aggtgtacac cctgccccca    720
tcccgggatg agctgaccaa gaaccaggtc agcctgacct gcctggtcaa aggcttctat    780
cccagcgaca tcgccgtgga gtgggagagc aatgggcagc cggagaacaa ctacaagacc    840
acgcctcccg tgctggactc cgacggctcc ttcttcctct acagcaagct caccgtggac    900
aagagcaggt ggcagcaggg gaacgtcttc tcatgctccg tgatgcatga ggctctgcac    960
aaccactaca cgcagaagag cctctccctg tctccgggta aatga                  1005
```

<210> SEQ ID NO 22
<211> LENGTH: 334
<212> TYPE: PRT
<213> ORGANISM: Artificial Sequence
<220> FEATURE:
<223> OTHER INFORMATION: amino acid sequence of VEGFR1-Fc

<400> SEQUENCE: 22

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Ala Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Glu Phe Glu Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
```

```
              195                 200                 205
Lys Val Ser Asn Lys Ala Leu Pro Ala Pro Ile Glu Lys Thr Ile Ser
            210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
290                 295                 300

Gln Gln Gly Asn Val Phe Ser Cys Ser Val Met His Glu Ala Leu His
                310                 315                 320

Asn His Tyr Thr Gln Lys Ser Leu Ser Leu Ser Pro Gly Lys
            325                 330

<210> SEQ ID NO 23
<211> LENGTH: 582
<212> TYPE: PRT
<213> ORGANISM: Artificial Sequence
<220> FEATURE:
<223> OTHER INFORMATION: SIRP alpha D1-Linker-anti-EGFR heavy chain

<400> SEQUENCE: 23

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Gly Gly Gly Ser Gly Gly Gly Ser
        115                 120                 125

Gly Gly Gly Gly Ser Gln Val Gln Leu Lys Gln Ser Gly Pro Gly Leu
    130                 135                 140

Val Gln Pro Ser Gln Ser Leu Ser Ile Thr Cys Thr Val Ser Gly Phe
145                 150                 155                 160

Ser Leu Thr Asn Tyr Gly Val His Trp Val Arg Gln Ser Pro Gly Lys
                165                 170                 175

Gly Leu Glu Trp Leu Gly Val Ile Trp Ser Gly Gly Asn Thr Asp Tyr
            180                 185                 190

Asn Thr Pro Phe Thr Ser Arg Leu Ser Ile Asn Lys Asp Asn Ser Lys
        195                 200                 205

Ser Gln Val Phe Phe Lys Met Asn Ser Leu Gln Ser Gln Asp Thr Ala
    210                 215                 220

Ile Tyr Tyr Cys Ala Arg Ala Leu Thr Tyr Tyr Asp Tyr Glu Phe Ala
```

```
            225                 230                 235                 240
Tyr Trp Gly Gln Gly Thr Leu Val Thr Val Ser Ala Ala Ser Thr Lys
                245                 250                 255
Gly Pro Ser Val Phe Pro Leu Ala Pro Ser Ser Lys Ser Thr Ser Gly
                260                 265                 270
Gly Thr Ala Ala Leu Gly Cys Leu Val Lys Asp Tyr Phe Pro Glu Pro
                275                 280                 285
Val Thr Val Ser Trp Asn Ser Gly Ala Leu Thr Ser Gly Val His Thr
            290                 295                 300
Phe Pro Ala Val Leu Gln Ser Ser Gly Leu Tyr Ser Leu Ser Ser Val
305                 310                 315                 320
Val Thr Val Pro Ser Ser Ser Leu Gly Thr Gln Thr Tyr Ile Cys Asn
                325                 330                 335
Val Asn His Lys Pro Ser Asn Thr Lys Val Asp Lys Arg Val Glu Pro
                340                 345                 350
Lys Ser Cys Asp Lys Thr His Thr Cys Pro Pro Cys Pro Ala Pro Glu
                355                 360                 365
Leu Leu Gly Gly Pro Ser Val Phe Leu Phe Pro Pro Lys Pro Lys Asp
            370                 375                 380
Thr Leu Met Ile Ser Arg Thr Pro Glu Val Thr Cys Val Val Val Asp
385                 390                 395                 400
Val Ser His Glu Asp Pro Glu Val Lys Phe Asn Trp Tyr Val Asp Gly
                405                 410                 415
Val Glu Val His Asn Ala Lys Thr Lys Pro Arg Glu Glu Gln Tyr Asn
            420                 425                 430
Ala Thr Tyr Arg Val Val Ser Val Leu Thr Val Leu His Gln Asp Trp
            435                 440                 445
Leu Asn Gly Lys Glu Tyr Lys Cys Lys Val Ser Asn Lys Ala Leu Pro
            450                 455                 460
Ala Pro Ile Ala Ala Thr Ile Ser Lys Ala Lys Gly Gln Pro Arg Glu
465                 470                 475                 480
Pro Gln Val Tyr Thr Leu Pro Pro Ser Arg Glu Glu Met Thr Lys Asn
                485                 490                 495
Gln Val Ser Leu Thr Cys Leu Val Lys Gly Phe Tyr Pro Ser Asp Ile
                500                 505                 510
Ala Val Glu Trp Glu Ser Asn Gly Gln Pro Glu Asn Asn Tyr Lys Thr
            515                 520                 525
Thr Pro Pro Val Leu Asp Ser Asp Gly Ser Phe Phe Leu Tyr Ser Lys
            530                 535                 540
Leu Thr Val Asp Lys Ser Arg Trp Gln Gln Gly Asn Val Phe Ser Cys
545                 550                 555                 560
Ser Val Met His Glu Ala Leu His Asn His Tyr Thr Gln Lys Ser Leu
                565                 570                 575
Ser Leu Ser Pro Gly Lys
            580

<210> SEQ ID NO 24
<211> LENGTH: 214
<212> TYPE: PRT
<213> ORGANISM: Artificial Sequence
<220> FEATURE:
<223> OTHER INFORMATION: Light chain of anti-EGFR antibody

<400> SEQUENCE: 24

Asp Ile Leu Leu Thr Gln Ser Pro Val Ile Leu Ser Val Ser Pro Gly
```

```
  1               5                  10                 15
Glu Arg Val Ser Phe Ser Cys Arg Ala Ser Gln Ser Ile Gly Thr Asn
                20                 25                 30

Ile His Trp Tyr Gln Gln Arg Thr Asn Gly Ser Pro Arg Leu Leu Ile
                35                 40                 45

Lys Tyr Ala Ser Glu Ser Ile Ser Gly Ile Pro Ser Arg Phe Ser Gly
                50                 55                 60

Ser Gly Ser Gly Thr Asp Phe Thr Leu Ser Ile Asn Ser Val Glu Ser
 65                 70                 75                 80

Glu Asp Ile Ala Asp Tyr Tyr Cys Gln Gln Asn Asn Asn Trp Pro Thr
                85                 90                 95

Thr Phe Gly Ala Gly Thr Lys Leu Glu Leu Lys Arg Thr Val Ala Ala
                100                105                110

Pro Ser Val Phe Ile Phe Pro Pro Ser Asp Glu Gln Leu Lys Ser Gly
                115                120                125

Thr Ala Ser Val Val Cys Leu Leu Asn Asn Phe Tyr Pro Arg Glu Ala
                130                135                140

Lys Val Gln Trp Lys Val Asp Asn Ala Leu Gln Ser Gly Asn Ser Gln
145                 150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
                180                185                190

Ala Cys Glu Val Thr His Gln Gly Leu Ser Ser Pro Val Thr Lys Ser
                195                200                205

Phe Asn Arg Gly Glu Cys
                210

<210> SEQ ID NO 25
<211> LENGTH: 366
<212> TYPE: PRT
<213> ORGANISM: Artificial Sequence
<220> FEATURE:
<223> OTHER INFORMATION: SIRP alpha D1-Fc

<400> SEQUENCE: 25

Glu Glu Glu Leu Gln Val Ile Gln Pro Asp Lys Ser Val Ser Val Ala
 1               5                  10                 15

Ala Gly Glu Ser Ala Ile Leu His Cys Thr Val Thr Ser Leu Ile Pro
                20                 25                 30

Val Gly Pro Ile Gln Trp Phe Arg Gly Ala Gly Pro Ala Arg Glu Leu
                35                 40                 45

Ile Tyr Asn Gln Lys Glu Gly His Phe Pro Arg Val Thr Thr Val Ser
                50                 55                 60

Glu Ser Thr Lys Arg Glu Asn Met Asp Phe Ser Ile Ser Ile Ser Ala
 65                 70                 75                 80

Ile Thr Pro Ala Asp Ala Gly Thr Tyr Tyr Cys Val Lys Phe Arg Lys
                85                 90                 95

Gly Ser Pro Asp Thr Glu Phe Lys Ser Gly Ala Gly Thr Glu Leu Ser
                100                105                110

Val Arg Ala Lys Pro Ser Ala Pro Val Val Ser Gly Pro Ala Ala Arg
                115                120                125

Ala Thr Pro Gln His Glu Phe Glu Pro Lys Ser Cys Asp Lys Thr His
                130                135                140

Thr Cys Pro Pro Cys Pro Ala Pro Glu Leu Leu Gly Gly Pro Ser Val
```

```
145                 150                 155                 160
Phe Leu Phe Pro Pro Lys Pro Lys Asp Thr Leu Met Ile Ser Arg Thr
                165                 170                 175
Pro Glu Val Thr Cys Val Val Val Asp Val Ser His Glu Asp Pro Glu
                180                 185                 190
Val Lys Phe Asn Trp Tyr Val Asp Gly Val Glu Val His Asn Ala Lys
                195                 200                 205
Thr Lys Pro Arg Glu Glu Gln Tyr Asn Ser Thr Tyr Arg Val Val Ser
    210                 215                 220
Val Leu Thr Val Leu His Gln Asp Trp Leu Asn Gly Lys Glu Tyr Lys
225                 230                 235                 240
Cys Lys Val Ser Asn Lys Ala Leu Pro Ala Pro Ile Glu Lys Thr Ile
                245                 250                 255
Ser Lys Ala Lys Gly Gln Pro Arg Glu Pro Gln Val Tyr Thr Leu Pro
                260                 265                 270
Pro Ser Arg Asp Glu Leu Thr Lys Asn Gln Val Ser Leu Thr Cys Leu
                275                 280                 285
Val Lys Gly Phe Tyr Pro Ser Asp Ile Ala Val Glu Trp Glu Ser Asn
    290                 295                 300
Gly Gln Pro Glu Asn Asn Tyr Lys Thr Thr Pro Pro Val Leu Asp Ser
305                 310                 315                 320
Asp Gly Ser Phe Phe Leu Tyr Ser Lys Leu Thr Val Asp Lys Ser Arg
                325                 330                 335
Trp Gln Gln Gly Asn Val Phe Ser Cys Ser Val Met His Glu Ala Leu
                340                 345                 350
His Asn His Tyr Thr Gln Lys Ser Leu Ser Leu Ser Pro Gly
                355                 360                 365
```